(12) United States Patent
Sperl et al.

(10) Patent No.: US 12,223,652 B2
(45) Date of Patent: Feb. 11, 2025

(54) METHOD FOR ASSIGNING A MEDICAL IMAGE DATASET TO A MEDICAL COMPARISON IMAGE DATASET DEPENDING ON BIOMETRIC DATA

(71) Applicant: Siemens Healthineers AG, Forchheim (DE)

(72) Inventors: Jonathan Sperl, Bamberg (DE); Michael Zenge, Nuremberg (DE); Jens Kaftan, Bamberg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 342 days.

(21) Appl. No.: 17/749,353

(22) Filed: May 20, 2022

(65) Prior Publication Data

US 2022/0383499 A1    Dec. 1, 2022

(30) Foreign Application Priority Data

May 25, 2021    (EP) ..................... 21175587

(51) Int. Cl.
*G06T 7/00* (2017.01)
*G06V 40/50* (2022.01)
*G16H 30/40* (2018.01)

(52) U.S. Cl.
CPC ............ *G06T 7/0016* (2013.01); *G06V 40/50* (2022.01); *G16H 30/40* (2018.01); *G06T 2207/30196* (2013.01)

(58) Field of Classification Search
CPC ........ G06T 7/0016; G06T 2207/30196; G16H 30/40; G06V 40/50
See application file for complete search history.

(56) References Cited

U.S. PATENT DOCUMENTS

| | | | |
|---|---|---|---|
| 10,997,715 B2 * | 5/2021 | Kelley, Jr. ............. | G06T 7/0014 |
| 2010/0307516 A1 | 12/2010 | Uhing et al. | |
| 2020/0193592 A1 * | 6/2020 | Arienzo ............... | A61B 5/0071 |
| 2021/0166406 A1 * | 6/2021 | Sperl ..................... | G16H 30/20 |

OTHER PUBLICATIONS

Ghesu Florin C.et al: "Multi-Scale Deep Reinforcement Learning for Real-Time 3D-Landmark Detection in CT Scans", IEEE Transactions on Pattern Analysis and Machine Intelligence, vol. 41, No. 1, Jan. 1, 2019, pp. 176-189, XP055725456.

* cited by examiner

*Primary Examiner* — Khai M Nguyen
(74) *Attorney, Agent, or Firm* — Harness, Dickey & Pierce, P.L.C.

(57) ABSTRACT

At least one example embodiment relates to a computer-implemented method comprising receiving a medical image dataset; receiving at least one medical comparison image dataset; extracting biometric data based on the medical image dataset; extracting biometric comparison data based on the medical comparison image dataset; determining a measure of difference between the biometric comparison data and the biometric data; and assigning the medical image dataset to the medical comparison image dataset when the measure of difference does not exceed a threshold value.

20 Claims, 5 Drawing Sheets

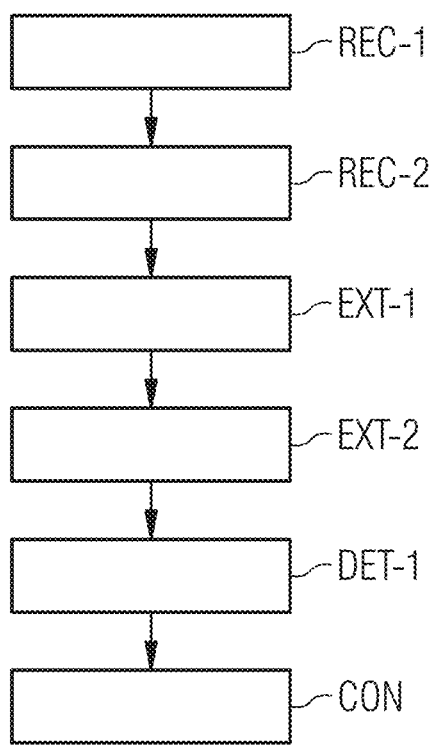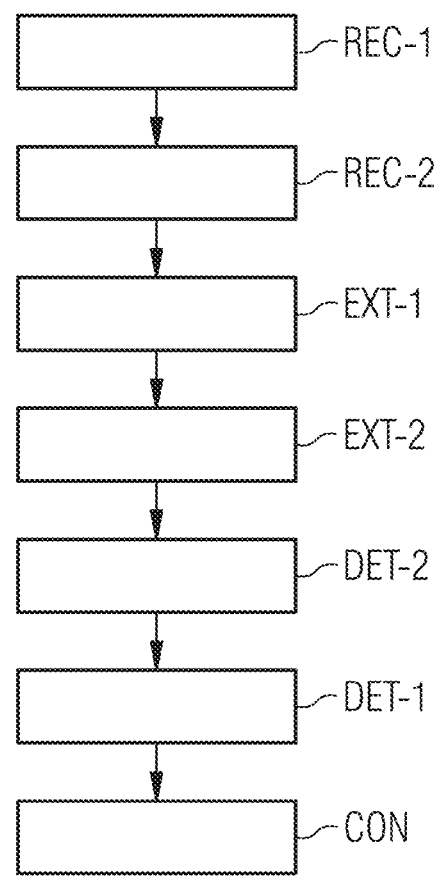

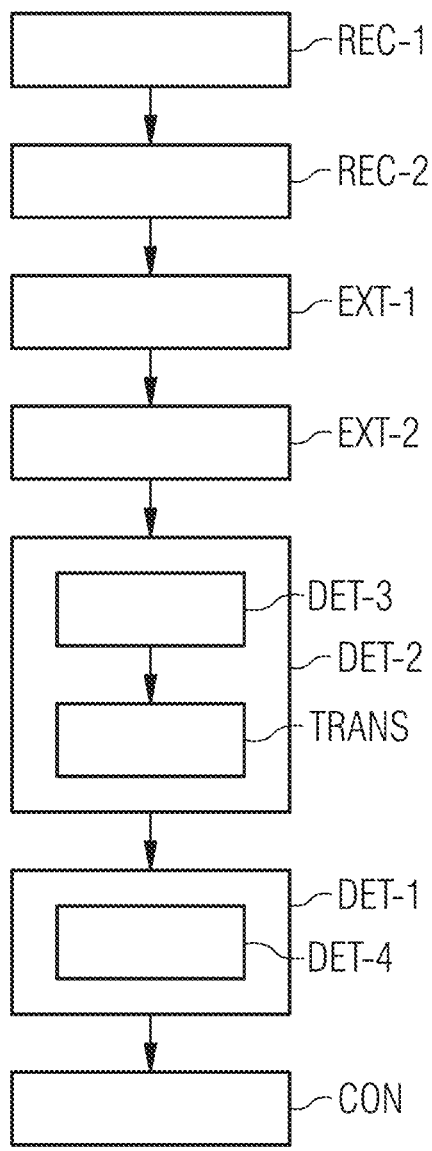
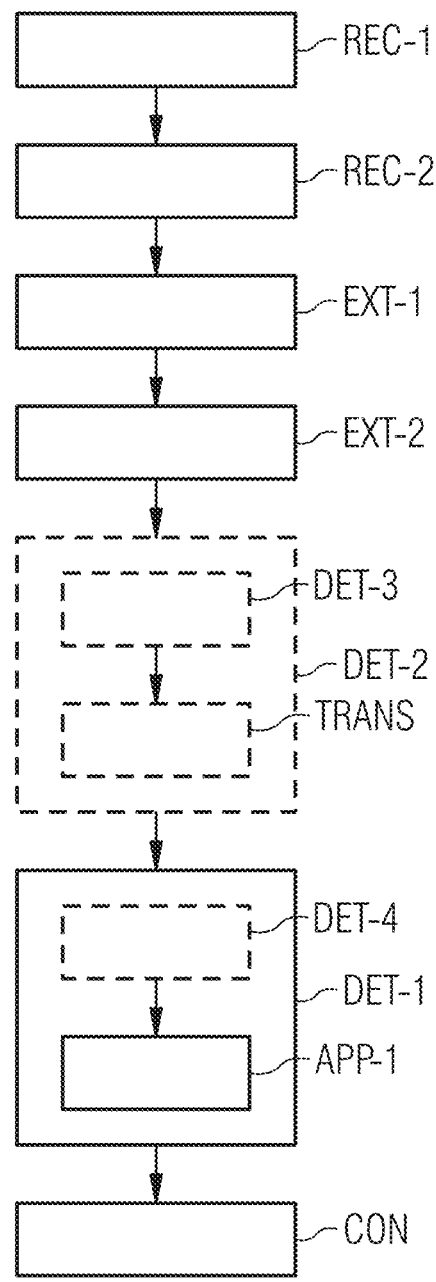

METHOD FOR ASSIGNING A MEDICAL IMAGE DATASET TO A MEDICAL COMPARISON IMAGE DATASET DEPENDING ON BIOMETRIC DATA

CROSS-REFERENCE TO RELATED APPLICATION(S)

The present application hereby claims priority under 35 U.S.C. § 119 to European patent application number EP 21175587.1 filed May 25, 2021, the entire contents of which are hereby incorporated herein by reference.

Frequently in medical imaging a plurality of medical image datasets is acquired from a patient. The medical image datasets can have been acquired in such cases at different points in time. Typically in such cases each imaging dataset comprises a map or a medical image of at least one part of the patient. In particular in such cases at least a part of the plurality of medical image datasets comprises a medical image of a pathology, for example a tumor, of the patient. The part of the plurality of medical image datasets in this case can map a change of the pathology over time. In other words, with the aid of the part of the plurality of medical image datasets a longitudinal or temporal analysis of a change in the pathology can be carried out.

Typically in a medical facility, for example a clinic and/or a medical practice, a plurality of image datasets from a plurality of patients is acquired, stored and/or analyzed.

In order to make a simple analysis of the medical image datasets possible, it is necessary to be able to assign the medical image datasets of a patient to one another. In particular it is advantageous for a user to be able to choose the patient for which the analysis is to be carried out and for the medical image datasets that are assigned to the patient to be taken into consideration automatically during the analysis. If a new medical image dataset of the patient is acquired, said dataset should be assigned to the plurality of medical image datasets that have already been acquired from the patient and are already assigned to one another.

At the same time it should be ensured that a medical image dataset from another patient is not incorrectly taken into consideration in the analysis.

Moreover it would be advantageous if the user were to be informed when the difference between the individual medical image datasets of the one patient assigned to one another is too great to enable a sensible longitudinal analysis to be carried out. A difference that is too great or a large variation between the medical image datasets can indicate that the patient has changed greatly, for example through a change in their weight and/or through an abnormal change in their pathology. As an alternative a difference that is too great or a change can indicate that at least one the medical image datasets assigned to one another is from another patient or comprises a medical image of another patient.

The plurality of medical image datasets of a patient is typically held in a database. Typically the database comprises medical image data from a plurality of patients. The medical image datasets are frequently analyzed in a Cloud system. For this the image datasets to be analyzed are uploaded into the Cloud system.

It is known that a medical image dataset can comprise patient data. The patient data enables the patient to be identified whose medical image or map the medical image dataset comprises. Typically this patient data is comprised by a DICOM (acronym for Digital Imaging and Communications in Imaging) header. The patient data for example comprises a name, a date of birth and/or a patient identification number (for example a medical insurance identification number) of the patient. It is known that the medical image datasets of a patient can be assigned to one another manually or automatically based on this patient data.

In an emergency situation the patient data will frequently not be acquired correctly, which makes it frequently impossible or complicated to assign the medical image dataset acquired in the emergency situation to a medical image dataset of the same patient already acquired beforehand.

In order to guarantee data protection a medical image dataset is pseudonymized or anonymized immediately before being uploaded into the Cloud system. In some versions the medical image datasets are already pseudonymized or anonymized in the database. In pseudonymization or anonymization of a medical image dataset patient data, which allows the identity of the patient to be deduced, is replaced by a pseudonym or is removed from the medical image dataset.

For this reason it is frequently not possible to assign the pseudonymized or anonymized medical image datasets of a patient to one another based on the patient data.

As an alternative patient data can be encrypted before being uploaded into the Cloud system or can already be encrypted in the database. In such cases the patient data of medical image datasets that have been acquired with different imaging systems is frequently encrypted by different algorithms. Thus it is not possible to assign to one another the patient data encrypted in a different way.

SUMMARY

It is known that in these cases the user manually selects the medical image datasets of the patient that are to be analyzed. In other words the user can assign the medical image datasets of a patient to one another manually. This process is very susceptible to errors, however.

At least one example embodiment provides a method that makes it possible to assign medical image datasets of a patient independently of the patient data and reliably.

This may be achieved by a method for assigning a medical image dataset to a medical comparison image dataset depending on biometric data, by an apparatus for assigning a medical image dataset to a medical comparison image dataset depending on biometric data, by a computer program product and by a computer-readable storage medium as claimed in the independent claims. Advantageous developments are given in the dependent claims and in the description below.

An inventive way in which the object is achieved is described below both with regard to the claimed apparatuses and also with regard to the claimed method. Features, advantages or alternate forms of embodiment are likewise also to be transferred to the other claimed subject matter and vice versa. In other words the physical claims (which are directed to an apparatus for example) are also developed with the features that are described or claimed in conjunction with a method. The corresponding functional features of the method are embodied in such cases by corresponding physical modules.

At least one example embodiment provides a computer-implemented method comprising receiving a medical image dataset; receiving at least one medical comparison image dataset; extracting biometric data based on the medical image dataset; extracting biometric comparison data based on the medical comparison image dataset; determining a measure of difference between the biometric comparison data and the biometric data; and assigning the medical image dataset to the medical comparison image dataset when the measure of difference does not exceed a threshold value.

According to at least one example embodiment, at least one of (i) the medical comparison image dataset maps at least one part of a body of a first patient, or (ii) the medical image dataset maps at least one part of the body of the first patient or a second patient.

According to at least one example embodiment, the biometric data comprises at least one of at least one anatomical landmark or at least one surface network of at least one anatomy of the mapped part of the body in the medical image dataset, and the biometric comparison data comprises at least one of at least one anatomical landmark or at least one surface network of at least one anatomy of the mapped part of the body in the medical comparison image dataset.

According to at least one example embodiment, at least one of the anatomical landmark or the surface network comprises at least one coordinate in the medical image dataset or in the medical comparison image dataset.

According to at least one example embodiment, the method includes establishing a registration between the biometric comparison data and the biometric data, and the determining the measure of difference is based on the registration.

According to at least one example embodiment, the establishing the registration includes determining at least one of anatomical landmarks or surface networks corresponding to one another in the biometric comparison data and the biometric data, and transforming the at least one of anatomical landmarks or surface networks corresponding to one another into a common coordinate system, and the determining the measure of difference includes determining a difference of the coordinates of the anatomical landmarks or surface networks corresponding to one another in the common coordinate system.

According to at least one example embodiment, the establishing the registration of the biometric comparison data and of the biometric data comprises a rigid registration.

According to at least one example embodiment, the determining the measure of difference comprises applying a trained function to the biometric comparison data and the biometric data to determine the measure of difference.

According to at least one example embodiment, the determining the measure of difference is based on a temporal stability of the at least one of at least one anatomical landmark or at least one surface network.

According to at least one example embodiment, the assigning the medical image dataset comprises at least one of creating a linkage between the medical image dataset and the medical comparison image dataset in a database; determining a common identification number for the medical image dataset and the medical comparison image dataset; or applying a function for image analysis to the medical comparison image dataset and the medical image dataset.

According to at least one example embodiment, the medical comparison image dataset has been acquired at a time before the medical image dataset, and the applying the function for image analysis to the medical comparison image dataset and the medical image dataset includes determining a temporal change between the medical comparison image dataset and the medical image dataset.

According to at least one example embodiment, the medical image dataset is assigned to the medical comparison image dataset by a provisional assignment, the method further comprising correcting the provisional assignment between the medical image dataset and the medical comparison image dataset when the measure of difference is greater than or equal to the threshold value.

According to at least one example embodiment, the method further includes providing a warning signal when the measure of difference is greater than or equal to threshold value.

At least one example embodiment provides an assignment system comprising an interface configured to receive a medical image data set and at least one medical comparison image; and a computing unit, the computing unit configured to extract biometric data based on the medical image dataset, extract biometric comparison data based on the medical comparison image dataset, determine a measure of difference between the biometric comparison data and the biometric data, and assign the medical image dataset to the medical comparison image dataset when the measure of difference does not exceed a threshold value.

At least one example embodiment provides a computer program or computer-readable storage medium comprising program sections, when executed by an assignment system, cause the assignment to perform a method according to at least one example embodiment.

At least one example embodiment provides an assignment system comprising an interface configured to obtain a medical image data set and at least one medical comparison image; and at least one processor configured to cause the assignment system to extract biometric data based on the medical image dataset, extract biometric comparison data based on the medical comparison image dataset, determine a measure of difference between the biometric comparison data and the biometric data, and assign the medical image dataset to the medical comparison image dataset when the measure of difference does not exceed a threshold value.

BRIEF DESCRIPTION OF THE DRAWINGS

Example embodiments of the invention will now be described and explained in greater detail making reference to the exemplary embodiments illustrated in the figures. In principle, structures and units which remain substantially the same are identified in the following description of the figures with the same reference characters as on the first occurrence of the relevant structure or unit.

FIG. 1 shows a first exemplary embodiment of a computer-implemented method for assigning a medical image dataset to a medical comparison image dataset depending on biometric data, FIG. 2 shows a second exemplary embodiment of a computer-implemented method for assigning a medical image dataset to a medical comparison image dataset depending on biometric data, FIG. 3 shows a third exemplary embodiment of a computer-implemented method for assigning a medical image dataset to a medical comparison image dataset depending on biometric data, FIG. 4 shows a fourth exemplary embodiment of a computer-implemented method for assigning a medical image dataset to a medical comparison image dataset depending on biometric data.

DETAILED DESCRIPTION

Figure 5:
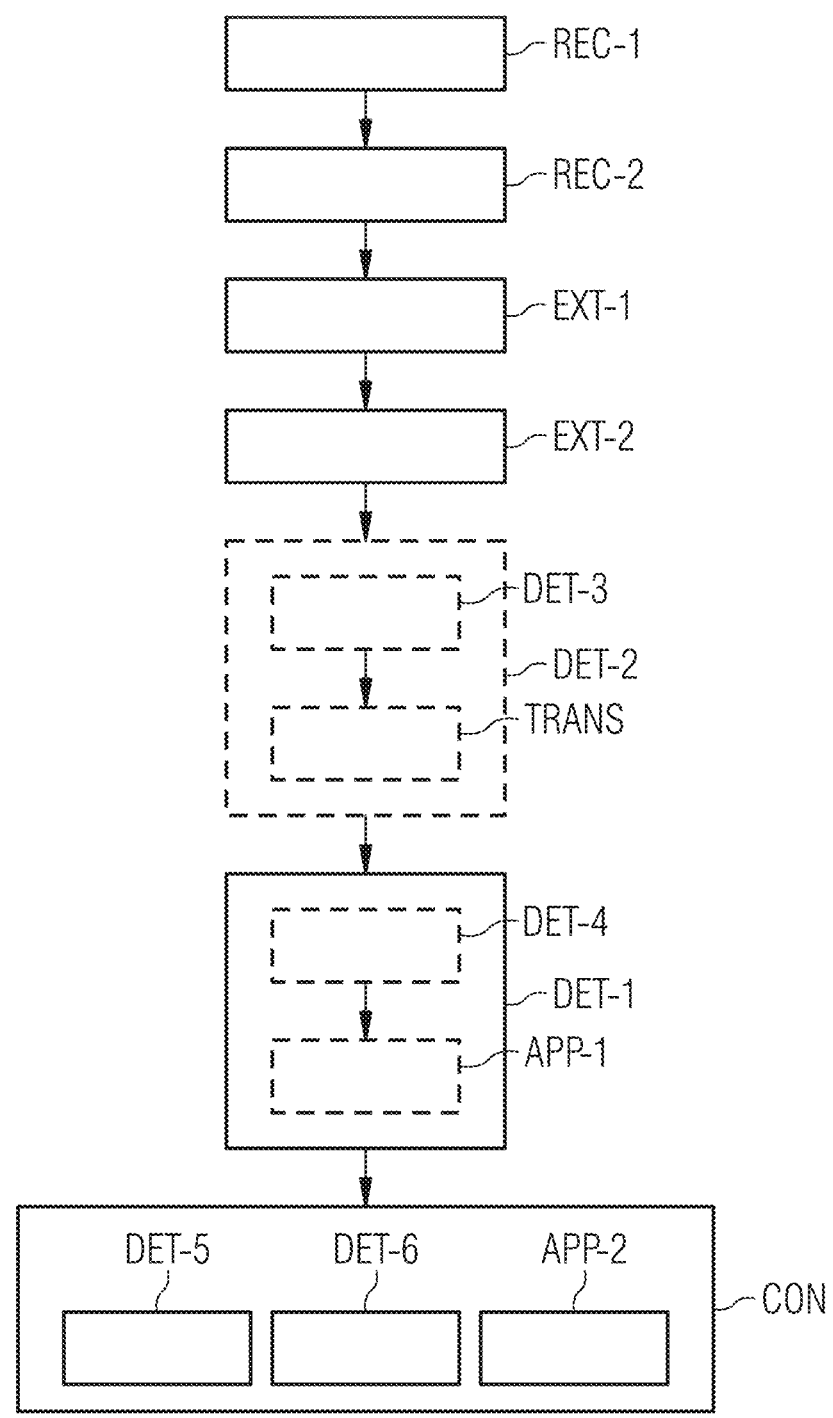
FIG. 5 shows a fifth exemplary embodiment of a computer-implemented method for assigning a medical image dataset to a medical comparison image dataset depending on biometric data.

At least one example embodiment of the invention relates to a computer-implemented method for assigning a medical image dataset to a medical comparison image dataset depending on biometric data. The method comprises a method step of receiving the medical image dataset. The method further comprises a method step of receiving a medical comparison image dataset. The method furthermore comprises a method step of extracting biometric data based on the medical image dataset. The method furthermore comprises a method step of extracting biometric comparison data based on the medical comparison image dataset. The method furthermore comprises a method step of determining a measure of difference between the biometric comparison data and the biometric data. The method furthermore comprises a method step of assigning the medical image dataset to the medical comparison image dataset when the measure of difference does not exceed a threshold value.

The medical image dataset comprises an image of a patient. In particular the medical image dataset comprises an image of a part of the patient. The part of the patient can in particular be a part of the body, for example a head, a thorax, an abdomen, an arm and/or a leg etc. of the patient. The image in this case is a medical image of the patient or of the part of the patient. The term "the medical image dataset maps the patient" is used synonymously below with "the medical image comprised by the medical image dataset maps a part of the patient or the patient". The medical image dataset is acquired in this case with a medical imaging system. The medical imaging system can in particular be an x-ray system, a mammography system, a computed tomography system, a magnetic resonance tomography system, a C-arm system, an ultrasound system, a positron emission tomography system or a single photon emission computed tomography system etc. The image or the medical image can thus be a pixelated or voxelated image. In other words the medical image comprises a two-dimensional pixel matrix or a three-dimensional voxel matrix. In this case each pixel or voxel is assigned a pixel value or voxel value. In other words the medical image can be a three-dimensional or a two-dimensional medical image. The medical image dataset can in particular be anonymized or pseudonymized or encrypted. In other words the medical image dataset can be embodied in such a way that it does not comprise any patient data that allows an identification of the patient shown in the medical image comprised by the medical image dataset. The patient data can for example comprise a name, a gender, a date of birth, an address, a patient-specific identification number etc. In a pseudonymization the patient data that allows the patient to be deduced can be replaced by a generic value. In anonymization patient data that allows the patient to be deduced can be removed or deleted. In encryption the patient data that allows the patient to be deduced can be encrypted in such a way that the patient data is only able to be decrypted into plain text data with the aid of at least one key. The encryption can depend on the imaging system with which the medical image dataset was acquired.

The medical comparison image dataset is embodied in a similar way to the medical image dataset. The medical comparison image dataset in this case can comprise a medical image or a map of the same patient as the medical image dataset. As an alternative the medical comparison image dataset can comprise a medical image of a different patient from the medical image dataset. The medical comparison image dataset in a medical image can map the same part of a patient as the medical image dataset. As an alternative the medical comparison image dataset can map a different part of a patient from the medical image dataset. The medical comparison image dataset can have been acquired with the same or with a different imaging system as the medical image dataset. The term "the medical comparison image dataset maps the patient" is used synonymously to "the medical image or map comprised by the medical comparison image dataset maps a part of the patient or the patient". The medical comparison image dataset can in particular be anonymized or pseudonymized or encrypted.

In the method steps of receiving the medical image dataset and receiving at least one medical comparison image dataset the medical image dataset and the medical comparison image dataset are received by an interface. The medical image dataset and/or the medical comparison image dataset can be provided in this case by the medical imaging system with which they were acquired. In other words the medical image dataset and/or the medical comparison image dataset can be received by the interface from the corresponding medical imaging system. As an alternative the medical image dataset and/or the medical comparison image dataset can be provided from a database. In other words the medical image dataset and/or the medical comparison image dataset can be received by the interface from the database. In particular the medical comparison image dataset and/or the medical image dataset can be held or stored in the database. The database can in particular be held or stored on a local server or in a Cloud system. The database in this case can in particular be a Picture Archiving and Communication System, acronym: PACS), a Hospital Information system (acronym: HIS) and/or a Radiology Information System (acronym: RIS) etc.

The term "image datasets" below refers to the medical image dataset and the medical comparison image dataset.

In the method step of extracting biometric data the biometric data is extracted based on the medical image dataset. In other words the biometric data is extracted depending on the medical image dataset. In this case the medical image dataset can comprise the biometric data. In the step of extracting the biometric data said data is then read out from the medical image dataset. As an alternative the biometric data can be determined based on the medical image dataset. In other words the extraction of the biometric data can comprise a determination of the biometric data. In particular the biometric data can be determined depending on the map or medical image comprised by the medical image dataset. In particular the biometric data can be established, extracted and/or computed based on or from the image data or medical image or map contained in the medical image dataset or in the medical comparison image dataset. In particular computer-implemented means or methods for, in particular automatic, image data analysis can be used for this which, in accordance with exemplary embodiments, can be implemented as computer program products.

The biometric data can in particular describe an anatomical characteristic of the patient whose medical image is comprised by the medical image dataset. Like a fingerprint of an individual describes a unique characteristic of the skin structure on a finger, the biometric data describes an individual, unique characteristic of the anatomy of the patient. For example the biometric data can describe or comprise a shape of an organ and/or a location of various organs in relation to one another and/or an characteristic of a skeleton or of a part of a skeleton and/or a shape of cerebral gyri etc. In alternate embodiments the biometric data can specify at least one special feature of the patient. For example the biometric data can specify if the patient only has one kidney and/or has a bone break and/or a size of the patient able to be derived from the image etc.

In the method step of extracting the biometric comparison data the biometric comparison data is extracted based on the medical comparison image dataset. In other words the biometric comparison data is extracted depending on the medical comparison image dataset. The extraction in this case can be embodied as described with regard to the biometric data. In particular the extraction can comprise a reading out or a determination of the biometric comparison data.

The biometric comparison data is embodied in this case in a similar way to the biometric data. The biometric comparison data in this case describes an individual, unique characteristic of the anatomy of the patient mapped in the comparison medical image dataset comprised by the medical image.

In the method step of determining the measure of difference the measure of difference between the biometric comparison data and the biometric data is determined. The measure of difference in this case determines how greatly the biometric data differs from the biometric comparison data. The measure of difference can for example specify as a percentage how great the difference is. As an alternative or in addition the measure of difference can specify the difference as a real number that describes a difference between the biometric data and the biometric comparison data. For example the real number can specify a difference in millimeters or centimeters. As an alternative or in addition the measure of difference can specify the difference in categorized form. For example the difference between the biometric data and the biometric comparison data can be divided into the categories or classes "large difference", "medium", "hardly any differences" or "3", "2", "1". The measure of difference then specifies the category into which the difference of the biometric data and the biometric comparison data was divided or categorized. The categories can be arranged hierarchically in this case. In this arrangement the categories that stand for a small difference can be arranged below the categories that stand for a large difference.

In the method step of assigning the medical image dataset to the medical comparison image dataset, the medical image dataset is assigned to the medical comparison image dataset when the measure of difference does not exceed the threshold value.

The threshold value specifies how great the measure of difference may be at a maximum so that it can be assumed that the medical image comprised by the medical image dataset and the medical image comprised by the medical comparison image dataset are images of the same patient. In particular the threshold value specifies how great the measure of difference may be at its maximum so that a further analysis, in particular a comparison the medical image of the medical image dataset and the medical image of the medical comparison image dataset is possible. The threshold value can specify, depending on the characteristic of the measure of difference, a percentage value, a real number and/or a category. The threshold value can in particular have been determined empirically.

When the measure of difference does not exceed the threshold value the medical image dataset is assigned to the medical comparison image dataset. When the measure of difference does not exceed the threshold value it can be assumed that the medical image dataset and the medical comparison image dataset are images of the same patient. In other words the medical images comprised by the medical image dataset and the medical comparison image dataset map the same patient when the measure of difference does not exceed the threshold value.

The assignment means in this case that, for a subsequent processing or analysis or display of the medical image dataset and the medical comparison image dataset, the information held is that both image datasets are images of the same patient. In other words the assignment specifies that the medical image dataset and the medical comparison image dataset are interrelated. For example a link between the medical image dataset and the medical comparison image dataset can be held in the database for this. In particular the effect of the assignment can be that, when an image dataset is retrieved, the assigned imaging dataset is likewise automatically retrieved. In other words the medical image dataset is retrieved when the medical comparison image dataset is retrieved and the medical image dataset is assigned to the medical comparison image dataset. Retrieval can mean here that the retrieved imaging dataset is to be used for a processing and/or an analysis and/or a display.

The inventors have recognized that biometric data can be extracted from a medical image dataset. In such cases the biometric data is based on a map or medical image comprised by the imaging dataset. The inventors have recognized that a patient is able to be identified with the aid of such biometric data. The inventors have thus recognized that, with the aid of the biometric data in the medical image of the medical image dataset and the biometric comparison data of the medical comparison image dataset, it can be recognized whether the two medical images are images of the same patient. The inventors have recognized that in this way it can be determined in an automated manner whether the image datasets are images of the same patient or of a similar patient with which a comparison with the patient to be diagnosed is sensible. The inventors have recognized that this can occur as a function of whether patient data comprised by the image datasets is anonymized or pseudonymized or encrypted. In other words an assignment of image datasets that map the same patient is possible without the patient data.

According to one example embodiment of the invention the medical comparison image dataset maps at least one part of the body of a first patient. As an alternative or in addition the medical image dataset maps at least one part of the body of a first patient or of a second patient.

As described above, "the medical comparison image dataset maps at least one part of the body", means that the medical comparison image dataset comprises a medical image that maps the at least one part of the body. Similarly "the medical image dataset maps at least one part of the body" means that the medical image dataset comprises a medical image that maps the at least one part of the body.

The at least one part of the body can be at least one part of the first or second patient. In particular the at least one part of the body can be the entire first or second patient. As an alternative the at least one part of the body can for example be the head, the thorax, the abdomen, a leg, an arm etc. of the first or second patient. In particular the medical comparison image dataset or the medical image dataset can map more than one part of the body. For example the medical comparison image dataset or the medical image dataset can map the thorax and the abdomen of the first or second patient.

In particular the medical comparison image dataset and the medical image dataset can map at least one part of the body of the same, in particular of the first, patient. In this case the medical comparison image dataset and the medical image dataset can map the same at least one part of the body of the first patient. As an alternative the medical comparison image dataset can map at least one other part of the body of the first patient as the medical image dataset.

As an alternative the medical comparison image dataset and the medical image dataset can each map at least one part of the body of different patients. In this case the medical comparison image dataset can map at least one part of the body of the first patient, while the medical image dataset maps at least one part of the body of the second patient. In this case the first and the second patient are different. In this case the at least one mapped part of the body in the medical comparison image dataset and the medical image dataset can be different. As an alternative the medical comparison image dataset and the medical image dataset can map the same at least one part of the body of two different patients.

The wording "the medical image dataset relates to the first or second patient" means below that the medical image dataset maps at least one part of the body of the first or second patient. Similarly the wording "the medical comparison image dataset relates to the first patient" means that the medical comparison image dataset maps at least one part of the body of the first patient.

The inventors have recognized that in particular a medical image of at least one part of the body of a patient is suitable for extracting biometric data or biometric comparison data. In other words the inventors have recognized that in particular, based on a medical image of at least one part of the body, the biometric data or biometric comparison data of the patient whose body part is mapped can be determined. The biometric data or biometric comparison data in this case is predetermined or defined or determined by the at least one part of the body mapped in the medical image dataset or medical comparison image dataset.

According to a further example embodiment of the invention the biometric data comprises at least one anatomical landmark and/or at least one surface network of at least one anatomy of the mapped part of the body in the medical image data. In this case the biometric comparison data comprises at least one anatomical landmark and/or at least one surface network of at least one anatomy of the mapped part of the body in the medical comparison image dataset.

The at least one anatomical landmark in this case specifies a position of an anatomy in the corresponding imaging dataset in particular in the medical image dataset or in the medical comparison image dataset. In other words the anatomical landmark specifies the position of the anatomy in the medical image comprised by the medical image dataset or the medical comparison image dataset. In other words the anatomical landmark describes or relates to the anatomy. The anatomy, of which the position is described by the anatomical landmark, can for example be one of the following anatomies: Center of the aortic arch, aortic root, branch of the arteria brachiocephalica, branch of the left arteria subclavia and the arteria vertebralis, branch of the right arteria subclavia and the arteria vertebralis, truncus coeliacus, left carotid artery, carina tracheae, heart, upper tip of the left kidney, upper tip of the right kidney, upper tip of the left lung, upper tip of the right lung, center of the liver, upper tip of the liver, pancreas, exit of the kidney artery, tip of the sternum, vertebral bodies: C7, T1, T2, T3, T4, T5, T6, T7, T8, T9, T10, T11, T12, L1.

The at least one anatomical landmark in the medical comparison image dataset or in the medical image dataset can have been determined for example as described in "Ghesu F C, Georgescu B, Zheng Y, Grbic S, Maier A, Hornegger J, Comaniciu D, "Multi-Scale Deep Reinforcement Learning for Real-Time 3D-Landmark Detection in CT Scans", IEEE Trans Pattern Anal Mach Intell. 2017".

The at least one surface network describes a surface of an anatomy in the medical image dataset or in the medical comparison image dataset. In other words the at least one surface network describes the surface of the anatomy in the medical image comprised by the medical image dataset or the medical comparison image dataset. The surface network in this case can comprise a plurality of points on the surface of the anatomy in the medical image. The anatomy in this case can for example be the left upper lobe of the lung, the left lower lobe of the lung, the right upper lobe of the lung, the right middle lobe of the lung, the right lower lobe of the lung, the heart, the aorta, the spinal column. The at least one surface network can have been determined based on a segmentation of the anatomy in the medical image.

The biometric data can in particular comprise anatomical landmarks of several different anatomies. As an alternative or in addition the biometric data can comprise surface networks of more than one anatomy. In such case two anatomical landmarks or surface networks can relate to different anatomies in each case. The biometric comparison data can in particular comprise anatomical landmarks of several different anatomies. As an alternative or in addition the biometric comparison data can comprise surface networks of more than one anatomy. In such cases two anatomical landmarks or surface networks can relate to different anatomies in each case.

In this case the at least one anatomical landmark or the at least one surface network of the biometric data can relate to the same anatomy as the at least one anatomical landmark or the at least one surface network of the biometric comparison data. As an alternative the at least one anatomical landmark or the at least one surface network of the biometric data can relate to a different anatomy from the at least one anatomical landmark or the at least one surface network of the biometric comparison data.

When the biometric data or the biometric comparison data comprises more than one anatomical landmark and/or more than one surface network, the biometric data or the biometric comparison data in particular also comprises information about a location of the individual anatomical landmarks and/or surface networks in relation to one another.

The inventors have recognized that the biometric data or the biometric comparison data of the first or second patient can be described by at least one anatomical landmark or at least one surface network. The inventors have recognized that the at least one anatomical landmark or the at least one surface network can map unique properties of the first or second patient. In particular the inventors have recognized that the location of a number of anatomical landmarks or surface networks in relation to one another maps the unique properties of the first or second patient especially well. In other words the location of the anatomical landmarks and/or surface networks in relation to one another or their spatial relationship are reasons for the uniqueness of the biometric data or the biometric comparison data for the first or second patient.

According to a further example embodiment of the invention the anatomical landmark and/or the surface network comprises at least one coordinate in the medical image dataset or in the medical comparison image dataset.

In this case the coordinate describes where in the medical image comprised by the medical image dataset or the medical comparison image dataset the anatomical landmark and/or the surface network lies. In this case the coordinate can for example specify a coordinate of the pixel or voxel in the corresponding medical image that maps the anatomical landmark or a point of the surface network. The coordinate of the pixel in this case is a pair of values that defines the location of the pixel in the pixel matrix. The coordinate of the voxel in this case is a triple that defines the location of the voxel in the voxel matrix.

In embodiments of the invention the medical image dataset can for example comprise a three-dimensional medical image and the medical comparison image dataset can comprise a two-dimensional medical image. The medical comparison image dataset thus comprises as its medical image or map of the patient a two-dimensional projection in an imaging plane. In particular the biometric data then comprises at least one triple, which defines the location of the at least one landmark in the medical image dataset. In particular the biometric comparison data then comprises at least one pair of values, which defines the location of the at least one landmark in the medical comparison image dataset. To be able to determine the measure of difference, the biometric data can be projected in a two-dimensional plane. In this case the two-dimensional plane can correspond to the imaging plane of the biometric comparison data. As an alternative the medical comparison image dataset can comprise a three-dimensional medical image and the medical image dataset a two-dimensional medical image. In this case the biometric comparison data can be projected in a two-dimensional plane.

The surface network in this case can comprise more than one coordinate. The coordinates are arranged in this case on a surface of the anatomy that is described by the surface network. In this case each coordinate of a surface network describes a point on the surface of the anatomy that is mapped or shown or described by the surface network.

When the biometric data or the biometric comparison data comprises more than one anatomical landmark and/or more than one surface network, a location of the anatomical landmarks and/or surface networks in relation to one another can be deduced from the coordinates of the individual anatomical landmarks and/or the surface networks. The location in relation to one another describes a spatial relationship of the anatomical landmarks and/or surface networks. The spatial relationship in this case can describe the distances between the individual anatomical landmarks and/or surface networks and/or the spatial arrangement of the anatomical landmarks and/or the surface networks in the two- or three-dimensional space. In particular the spatial relationship can also describe a shape of a surface network. The shape is predetermined in this case by the shape of the anatomy that the surface network describes.

Knowledge of a scale of the mapped part of the body in the medical image data or the medical comparison image data enables a distance between individual anatomical landmarks and/or points surface networks in a metric unit to be deduced. A metric unit can be millimeter, centimeter or meter for example. As an alternative the distance can be specified in an alternate distance unit for example in inch or foot. The spatial relationship in this case can define the location of the anatomical landmarks and/or surface networks in relation to one another in space.

In embodiments of the invention the coordinate can specify a location of the anatomical landmark or of a point of the surface network relative to the mapped part of the body. For example a "zero point" in the mapped part of the body can be predetermined. The zero point in this case can correspond to the origin of the coordinate system in which the coordinates are specified. The zero point can be arranged for example at a significant point. The zero point can for example be the xiphoid process or the center of the heart or the branch of the trachea etc. The zero point can in particular be an anatomical landmark. The coordinate of the anatomical landmark or of the surface network can then be specified in relation to the zero point. In this case the axes of the coordinate system can be arranged in parallel to the body axes of the patient. The body axes are in particular cranio-caudal, dorsal-frontal or posterior-anterior and lateral-medial. The coordinate in this case can specify the distance of the anatomical landmark or of the point of the surface network to the origin in metric units or an alternate distance unit.

The inventors have recognized that location relationships or spatial relationships of the anatomical landmarks and/or surface networks can be described with the aid of coordinates. Moreover the inventors have recognized that, based on the coordinates, distances between individual anatomical landmarks or points of a surface network can be determined. The inventors have recognized that in this way a generalization in a uniform measure of distance or a uniform distance unit, for example a metric unit, is possible. The inventors have recognized that this can be based on a coordinate system, of which the position of the origin is adapted to a position of the first or second patient in the medical image dataset or in the medical comparison image dataset. The inventors have recognized that two-dimensional and three-dimensional biometric data can be compared by a projection.

According to a further example embodiment of the invention the method comprises a method step of establishing a registration between the biometric comparison data and the biometric data. In this aspect the method step of determining the measure of difference is undertaken based on the registration.

In the method step of establishing the registration in particular the anatomical landmarks and/or surface networks of the biometric data and the biometric comparison data are put into a spatial relationship to one another. In particular the biometric data and the biometric comparison data can be positioned spatially relative to one another.

In particular the biometric data can comprise more than one anatomical landmark and/or more than one surface network. In this case two anatomical landmarks or surface networks relate to different anatomies in each case. In particular the biometric comparison data can comprise more than one anatomical landmark and/or more than one surface network. In this case two anatomical landmarks or surface networks relate to different anatomies in each case. In particular in this case the anatomical landmarks or surface networks of the biometric data and the biometric landmarks or surface networks of the biometric comparison data can at least partly relate to or describe the same anatomies. In other words at least one anatomical landmark or surface network of the biometric data can relate to the same anatomy as an anatomical landmark or a surface network of the biometric comparison data. During registration in particular the spatial relationship of the anatomical landmarks and/or surface networks of the biometric data and the spatial relationship of the anatomical landmarks and/or surface networks of the biometric comparison data can be retained or remain unchanged. Through the registration the anatomical landmarks and/or surface networks of the biometric data are positioned relative to the anatomical landmarks and/or surface networks of the biometric comparison data.

The measure of difference compares the position of an anatomical landmark of the biometric data and an anatomical landmark of the biometric comparison data that relate to the same anatomy in each case. As an alternative or in addition the measure of difference compares the shape and/or position of a surface network of the biometric data with the shape and/or position of a surface network of the biometric comparison data, which relate to the same anatomy. In particular the measure of difference compares the position and/or shape of all anatomical landmarks and/or surface networks of the biometric data and of the biometric comparison data which correspond to one another. Anatomical landmarks and/or surface networks which correspond to one another relate in such cases to the same anatomy.

The inventors have recognized that, based on a registration, a comparison of the positions of the anatomical landmarks and/or surface networks of the biometric data and of the biometric comparison data is possible. The inventors have recognized that the spatial relationship or location or arrangement of the anatomical landmarks and/or surface networks is unique to a specific patient.

The inventors have recognized that it is possible, based on the registration, to establish or to determine a measure of difference that specifies how strongly the positions and thereby the spatial relationship of the anatomical landmarks and/or surface networks of the biometric data differ from those of the biometric comparison data.

According to a further example embodiment of the invention the method step of establishing the registration comprises a method step of determining anatomical landmarks and/or surface networks in the biometric comparison data and the biometric data which correspond to one another and a method step of transforming the anatomical landmarks and/or surface networks which correspond to one another into a common coordinate system. In this case the method step of determining the measure of difference comprises a method step of determining a difference of the coordinates of the anatomical landmarks or surface networks which correspond to one another in the common coordinate system.

In the method step of determining anatomical landmarks and/or surface networks which correspond to one another at least one anatomical landmark and/or surface network of the biometric data is assigned to an anatomical landmark and/or surface network of the biometric comparison data that relates to the same anatomy or that describes its location or position. "Corresponding" in this case means that the anatomical landmarks or surface networks which correspond to one another relate to the same anatomy.

When the biometric data and/or the biometric comparison data comprises more than one anatomical landmark and/or surface network, the anatomical landmarks and/or surface networks of the biometric data and of the biometric comparison data can be assigned to one another at least partly in pairs. In this case anatomical landmarks and/or surface networks corresponding to one another, i.e. relating to the same anatomy, are assigned to one another.

In embodiments not every anatomical landmark and/or surface network can be assigned a corresponding anatomical landmark and/or surface network. These anatomical landmarks and/or surface networks can be ignored or not taken into consideration when determining the measure of difference.

In the method step of transforming the landmarks and/or surface networks corresponding to one another into a common coordinate system the at least one anatomical landmark and/or the at least one surface network of the biometric data is transformed into a common coordinate system with the at least one anatomical landmark and/or the at least one surface network of the biometric comparison data.

When the biometric data and/or the biometric comparison data comprises more than one anatomical landmark and/or more than one surface network, at least the anatomical landmarks and/or surface networks of the biometric data that have a corresponding equivalent in the biometric comparison data can be transformed into the common coordinate system. Similarly at least the anatomical landmarks and/or surface networks of the biometric comparison data that have a corresponding equivalent in the biometric data can be transformed into the common coordinate system. As an alternative all anatomical landmarks and/or surface networks of the biometric data and of the biometric comparison data can be transformed into the common coordinate system.

In particular during transformation into a common coordinate system the anatomical landmarks and/or surface networks of the biometric data can retain the spatial relationship to each other when the biometric data comprises more than one anatomical landmark and/or more than one surface network. Similarly the anatomical landmarks and/or surface networks of the biometric comparison data can retain the spatial relationship to one another when the biometric comparison data comprises more than one anatomical landmark and/or more than one surface network.

The common coordinate system in this case can map the spatial location or distribution of the anatomical landmarks and/or surface networks in relation to one another in a metric system. As an alternative the common coordinate system can map the spatial location or distribution in an alternate distance system for example the Anglo-American system of measurements.

In particular in the common coordinate system the at least one anatomical landmark and/or surface network of the biometric data can be positioned relative to the at least one landmark and/or surface network of the biometric comparison data.

During transformation in particular the spatial relationship or location or arrangement of the anatomical landmarks and/or surface networks of the biometric data can be adapted to a measure of the common coordinate system. Similarly the spatial location or arrangement of the anatomical landmarks and/or surface networks of the biometric comparison data can be adapted to a measure of the common coordinate system. The measure can in particular specify a distance measure or path measure. The measure is specified in this case in particular by the system or measurement system of the common coordinate system. The distance measure can be specified for example in metric units or in the Anglo-American system of measurements.

During transformation at least one anatomical landmark of the biometric data can be mapped to a corresponding anatomical landmark of the biometric comparison data in the common coordinate system. In particular this means that the two landmarks, if they correspond to one another, are set to the same position during transformation in a common coordinate system. As an alternative a surface network of the biometric data can be mapped to a surface network of the biometric comparison data. All other anatomical landmarks and/or surface networks of the biometric data and of the biometric comparison data are positioned according to the spatial relationship relative to the at least one anatomical landmark or surface network in the common coordinate system.

For example the two zero points of the biometric data and of the biometric comparison data described above can be mapped to one another or set to the same position in the common coordinate system when the two zero points relate to anatomical landmarks corresponding to one another.

In particular a pair of anatomical landmarks or surface networks can be used as a reference point or zero point for the transformation into a common coordinate system. In particular this pair can be positioned at a common position in the common coordinate system, for example the origin. All other anatomical landmarks and/or surface networks can retain their spatial relationship relative to the pair. The spatial relationship can be adapted in this case to the measure of the common coordinate system.

As an alternative, when the biometric data and the biometric comparison data each comprises more than one anatomical landmark and/or more than one surface network, the anatomical landmarks and/or surface networks of the biometric data can be positioned while retaining the spatial relationship relative to the anatomical landmarks and/or surface networks of the biometric comparison data in such a way in the common coordinate system that the distances of the positions of the respective corresponding anatomical landmarks and/or surface networks are minimized. In particular the sum or the quadratic sum of the distances can be minimized.

In the method step of determining a difference of the coordinates of the landmarks or surface networks corresponding to one another the difference of the positions of the anatomical landmarks or surface networks corresponding to one another is determined in the common coordinate system. In particular, for each pair of anatomical landmarks, a spatial distance of the positions can be determined in the common coordinate system. The measure of difference can in this case correspond to the sum of the distances of the individual pairs. As an alternative the measure of difference can correspond to the square root of the quadratic sum of the distances of the individual pairs. When the distances of the coordinates of more than one pair of anatomical landmarks and/or surface networks are determined, the measure of difference embodied as described above can be standardized by a division by the number of pairs.

In surface networks corresponding to one another the differences of the coordinates or points that define the surface networks can be determined. As an alternative each surface network can comprise an interpolated surface between the coordinates or points of the surface network. In particular the difference of the coordinates of two surface networks can then comprise a difference of the surfaces in the common coordinate system.

The inventors have recognized that a registration makes possible a comparison of the biometric data and of the biometric comparison data. The inventors have recognized that, when the registration comprises a transformation into a common coordinate system, a comparison of the spatial relationship of the at least one anatomical landmark and/or surface network comprised by the biometric data with the spatial relationship of the at least one anatomical landmark and/or surface network comprised by the biometric comparison data is made possible. The inventors have recognized that the measure of difference determined in this way specifies how well the spatial relationship of the anatomical landmarks and/or surface networks of the biometric data matches the spatial relationship of the anatomical landmarks and/or surface networks of the biometric comparison data.

According to a further example embodiment of the invention the establishing of the registration of the biometric comparison data and of the biometric data comprises a rigid registration.

In other words the registration is a rigid registration.

In particular the biometric data and the biometric comparison data each comprises more than one anatomical landmark and/or more than one surface network. In particular the anatomical landmarks and/or surface networks of the biometric data or of the biometric comparison data are in a spatial relationship or location or arrangement to one another. In other words the anatomical landmarks and/or surface networks of the biometric data or biometric comparison data are at defined distances from one another. The distances can be specified in such cases in metric units or in the Anglo-American system of measurements. The spatial relationship can also describe how the anatomical landmarks and/or surface networks are arranged relative to one another in a two-dimensional or three-dimensional space.

In the rigid registration the spatial relationship of the anatomical landmarks and/or surface networks of the biometric data is retained. Similarly in the rigid registration the spatial relationship of the anatomical landmarks and/or surface networks of the biometric comparison data is retained. In the rigid registration merely the distances between the anatomical landmarks and/or surface networks of the biometric data or of the biometric comparison data relative to one another are changed, i.e. all distances are changed to the same extent.

In an embodiment of the rigid registration an anatomical landmark or a surface network of the biometric data is thus mapped to the corresponding anatomical landmark or the corresponding surface network of the biometric comparison data. In other words an anatomical landmark or a surface network of the biometric data is positioned at the same position in the common coordinate system as the corresponding anatomical landmark or the corresponding surface network of the biometric comparison data. All other anatomical landmarks or surface networks are positioned in the common coordinate system with the aid of their spatial relationship to one another. Just the distances can be adapted to the scale of the common coordinate system.

In an alternate embodiment of the rigid registration the anatomical landmarks and/or surface networks are positioned as described above while retaining the spatial relationship in such a way in the common coordinate system that the distances between the anatomical landmarks and/or surface networks corresponding to one another is minimized. "Retention of the spatial relationship" also means here that only the distances between the anatomical landmarks and/or surface networks are adapted to the scale of the coordinate system. The absolute distances in a metric or Anglo-American unit are retained. Likewise the spatial arrangement in the two- or three-dimensional space is retained.

The inventors have recognized that a specific spatial relationship of the anatomical landmarks and/or surface networks is unique for a patient. The inventors have recognized that this spatial relationship is retained in a rigid registration. The inventors have recognized that it can be established in this way whether, because of the spatial relationship, it can be assumed that the biometric data originates or does not originate from a medical image of the same patient as the biometric comparison data.

According to a further example embodiment of the invention the method step of determining the measure of difference comprises a method step of applying a trained function to the biometric comparison data and the biometric data, whereby the measure of difference is determined.

In general a trained function imitates cognitive functions that connect human beings with human thought. In particular by training based on training data the trained function can adapt to new circumstances and also recognize and extrapolate patterns.

In general parameters of a trained function can be adapted by training. In particular a supervised training, a semi-supervised training, an unsupervised training, a reinforcement learning and/or an active learning can be used for this. Furthermore representation learning (an alternative term is feature learning) can be used. In particular the parameters of the trained functions can be adapted iteratively by a number of training steps.

In particular a trained function can comprise a neural network, a support vector machine, a random tree or a decision tree and/or a Bayesian network, and/or the trained function can be based on k-means clustering, Q-learning, genetic algorithms and/or association rules. In particular a trained function can comprise a combination of a number of uncorrelated decision trees or an ensemble of decision trees (random forest). In particular the trained function can be defined by XGBoosting (eXtreme Gradient Boosting). In particular a neural network can be a deep neural network, a convolutional neural network or a convolutional deep neural network. Furthermore a neural network can be an adversarial network, a deep adversarial network and/or a generative adversarial network. In particular a neural network can be a recurrent neural network. In particular a recurrent neural network can be a network with long short-term memory, (LSTM), in particular a Gated Recurrent Unit (GRU). In particular a trained function can comprise a combination of the approaches described. In particular the approaches described here for a trained function are called the network architecture of the trained function.

The trained function can thus be applied to the at least one anatomical landmark and/or the at least one surface network of the biometric data and the at least one anatomical landmark and the at least one surface network of the biometric comparison data. In this case the measure of difference is determined. The measure of difference in this case specifies how strongly the biometric data differs from the biometric comparison data. When the biometric data or the biometric comparison data comprises more than one anatomical landmark and/or more than one surface network, the measure of difference specifies how strongly the spatial relationship of the anatomical landmarks and/or of the surface networks of the biometric data differs from the spatial relationship of the anatomical landmarks and/or surface networks of the biometric comparison data. The spatial relationship can in this case, as described above, describe the distances between the individual anatomical landmarks and/or surface networks and/or the spatial arrangement of the anatomical landmarks and/or of the surface networks in two or three dimensions. In particular the spatial relationship can also describe a shape of a surface network. The shape is predetermined in this case by the shape of the anatomy that the surface network describes. In particular the measure of difference can thus describe the difference of the positions of the anatomical landmarks and/or surface networks of the biometric data and of the anatomical landmarks and/or surface networks of the biometric comparison data. In this case, in particular as described above, the positions of anatomical landmarks and/or surface networks corresponding to one another are compared.

In this case the measure of difference can specify how likely it is that the biometric data and the biometric comparison data originate from different patients. In other words the measure of difference can specify how likely it is that the medical image dataset maps the at least one part of the body of the second patient when the medical comparison image dataset maps the at least one part of the body of the first patient. The greater is the measure of difference, the more likely it is that the medical image dataset maps a different patient from the medical comparison image dataset.

The trained function can be trained with a plurality of biometric training data and biometric training comparison data. In this case the trained function is applied to a pair of biometric training data and biometric training comparison data in each case. In this case a training measure of difference is determined. Moreover a manual measure of difference between the biometric training data and the biometric training comparison data is determined beforehand. The training measure of difference is compared with the manually determined measure of difference. The parameters of the trained function are then adapted in such a way that, with a renewed application, the training measure of difference matches the manually determined measure of difference as well as possible. The manually determined measure of difference can in this case in particular be determined by an expert.

The inventors have recognized that the measure of difference is able to be determined with the aid of a trained function. The inventors have recognized that a registration can be dispensed with in this way. The inventors have recognized that errors that can occur in the transformation of the biometric data and of the biometric comparison data into the common coordinate system can be reduced when the measure of difference is determined with the trained function.

According to a further example embodiment of the invention an influence of the at least one anatomical landmark and/or of the at least one surface network on the measure of difference depends on their temporal stability.

The influence in this case describes a weighting with which the at least one anatomical landmark and/or the at least one surface network is taken into consideration when determining the measure of difference. The influence of an anatomical landmark or a surface can be defined for example by a weighting for example of the position of the anatomical landmark or of the surface network in the common coordinate system when determining the measure of difference.

For example the difference of the coordinates of two anatomical landmarks and/or surface networks which correspond to one another in the common coordinate system can be weighted when determining the measure of difference. The weighting in this case determines the influence of the anatomical landmarks and/or of the surface network on the measure of difference. When the biometric data or the biometric comparison data comprises more than one anatomical landmark and/or more than one surface network, the difference of the coordinates of two landmarks or surface networks corresponding to one another can be weighted depending on their temporal stability when determining the measure of difference. For this the difference of the coordinates can be multiplied by a weighting factor. The weighting factor can be different for different anatomical landmarks or surface networks. The measure of difference can then be the sum or the quadratic sum of the square root of the differences weighted in this way of all landmarks and/or surface networks corresponding to one another.

As an alternative a weighting of the individual anatomical landmarks and/or surface networks in the trained function can depend on the temporal stability. The trained function, when determining the measure of difference of temporally stable anatomical landmarks and/or surface networks, can be more heavily weighted than for temporally unstable anatomical landmarks and surface networks. A greater weighting in this case means a greater influence on the measure of difference.

Temporally stable means in this case that the anatomical landmark or the surface network does not change or changes little over time. A temporally stable anatomical landmark can for example involve a bone and/or vertebral bodies and/or the xiphoid process etc. With adult patients without any disease of the bone such as for example osteoporosis such anatomical landmarks are spatially and temporally almost unchanging.

A temporally non-stable anatomical landmark can involve a lower lung tip for example. In the course of breathing this permanently changes its position relative to a temporally stable anatomical landmark. This means that a difference of the position or of the coordinates of the lower lung tip between the biometric data and the biometric comparison data can mean that different patients are involved. As an alternative however the same patient at different times of a breathing interval can have been acquired in the medical image dataset and the medical comparison image dataset.

The same also applies to surface networks. A temporally stable surface network can for example describe a surface of a sternum. A temporally unstable surface network can for example be a surface of a lobe of the lung or the heart.

The inventors have recognized that a difference of temporally unstable anatomical landmarks and/or surface networks is less informative regarding the biometric properties of a patient than temporally stable anatomical landmarks and/or surface networks. The inventors have recognized that this can be taken into consideration by a weighting when determining the measure of difference. In other words the influence of the at least one anatomical landmark and/or of the at least one surface network of the biometric data or of the biometric comparison data on the measure of difference can be taken into consideration in the trained function by a weighting of the difference of the coordinates or by a weighting of the at least one anatomical landmark and/or surface network.

According to an optional example embodiment of the invention the method comprises a method step of classifying the at least one anatomical landmark and/or the at least one surface network according to their temporal stability. In this case the influence of the at least one anatomical landmark and/or of the at least one surface network on the measure of difference depends on the classification. In this case the classifying is based on a known anatomically-based behavior of the at least one anatomical landmark and/or of the at least one surface network.

The known anatomically based behavior is in particular known to a person skilled in the art. The person skilled in the art knows the temporal stability of different anatomies. Anatomically based means in this case that the temporal stability or the behavior is generally valid. In other words the reason for the temporal stability is the anatomy. In particular the reason for the temporal stability of the at least one anatomical landmark and/or of the at least one surface network can thus be given by the "task" of the corresponding anatomy.

For example it is known that an anatomical landmark or a surface network that relates to the lungs is temporally unstable, while an anatomical landmark or a surface network that relates to the sternum is temporally stable. The reason for the temporal instability of the lungs is the anatomically based behavior of the function of a "pair of bellows". The anatomically based behavior of the sternum, which brings about a stabilization of the chest cavity, is the reason for the temporal stability of the sternum.

Thus classes can be defined to which various anatomies are assigned. For example the skeleton, in particular the vertebral bodies and/or the sternum etc. can be assigned to a class with the designation "stable". For example the lungs and/or the heart can be assigned to a class with the designation "unstable". In particular at least one anatomical landmark and/or at least one surface network, which for example relates to the lungs and/or the heart, can be assigned to the class "unstable". For example the bowel or at least one anatomical landmark and/or at least one surface network that relates to the bowel can be assigned to a class with the designation "relatively stable".

Based on these predefined classes, the at least one anatomical landmark and/or the at least one surface network can be classified in the method step of classifying.

The influence of the at least one anatomical landmark or of the at least one surface network on the measure of difference depends on the corresponding temporal stability and thus on the class of the at least one anatomical landmark or of the at least one surface network.

The inventors have recognized that, to determine or classify the temporal stability, generally valid assumptions can be made. The inventors have recognized that it is not necessary to determine the temporal stability of an anatomical landmark and/or of a surface network for each patient once again in a longitudinal or temporal analysis of image data. The inventors have recognized that the method can be speeded up in this way. The inventors have moreover recognized that a good comparability is achieved by the classification based on expert knowledge or a generally valid assumption.

According to a further example embodiment of the invention the method step of assigning the medical image dataset comprises at least one of the following steps:

Creating a link between the medical image dataset and the medical comparison image dataset in a database;

Determining a common identification number for the medical image dataset and the medical comparison image dataset;

Applying a function for image analysis to the medical comparison image dataset and the medical image dataset.

In this case at least one of the said steps is carried out when the measure of difference does not exceed the threshold value. In particular it can then be assumed that the medical image dataset and the medical comparison image dataset are mapping the same, in particular the first, patient.

In the method step of creating a linkage, a link or a reference to a storage location of the other imaging dataset in each case can be added to the medical image dataset and/or the medical comparison image dataset. In other words a link to the storage location of the medical comparison image dataset can be added to the medical image dataset. As an alternative or in addition a link to the storage location of the medical image dataset can be added to the medical comparison image dataset. The storage location in this case can be defined as a location in the database. The location can be addressable via the link in this case. In other words the linkage can be a reference to the other imaging dataset in each case.

The database in this case can be embodied as described. In particular the database can be embodied for storing medical image datasets.

In the method step of determining a common identification number (acronym: ID) a common ID can be determined for the medical image dataset and the medical comparison image dataset. The ID in this case can assume a role of a patient identification number. The ID in this case is independent of the patient data and is only determined as a function of the measure of difference in comparison to the threshold value. The ID in this case can be a generic sequence of digits and/or numbers. The ID in this case is in particular unique. In other words an ID is uniquely assigned to a pair or a group of image datasets assigned to one another.

By a database query for the common ID for example all image datasets in the database assigned to one another can be provided automatically. In particular the medical image dataset and the medical comparison image dataset are then provided.

In the method step of applying a function for image analysis the function for image analysis is applied to the medical image dataset and the medical comparison image dataset. In this case the function for image analysis is applied when the measure of difference is below the threshold value. In other words the function for image analysis is applied when it is assumed that the medical image dataset and the medical comparison image dataset are mapping the same patient, in particular the first patient. By applying the function for image analysis for example the medical image dataset and the medical comparison image dataset can be compared. As an alternative or in addition, by applying the function for image analysis, the medical image dataset and the medical comparison image dataset can be registered.

The inventors have recognized that, depending on whether the medical image dataset and the medical comparison image dataset are mapping the same patient, various further method steps can be carried out. The inventors have recognized that data processing of the image datasets can be simplified through the linkage and/or the common ID. In particular it is possible in this way to structure data in the database and facilitate access. For example a user, for example a doctor or a medical assistant, can retrieve all images of a patient at once when the images are linked to one another via the linkage and/or the common ID. The user does not have to provide any patient data for this; it is sufficient for the user to select an imaging dataset of the patient. The other image datasets of the patient can then be retrieved via the link or the links and/or the ID. The inventors have recognized that an image analysis by applying a function for image analysis is only sensible when it can be assumed that the medical image dataset and the medical comparison image dataset are mapping the same patient.

According to a further example embodiment of the invention the medical comparison image dataset is acquired temporally before the medical image dataset. In this case, by the application of the function for image analysis to the medical comparison image dataset and the medical image dataset, a temporal change between the medical comparison image dataset and the medical image dataset can be determined.

The medical image dataset and the medical comparison image dataset in particular map the same patient in this case, in particular the first patient. In this case the measure of difference is in particular lower than the threshold value. The medical image dataset can have been acquired for example a week, a month, three months, six months, a year etc. after the medical comparison image dataset. In particular the medical image dataset can have been acquired within the course of a follow-up examination of the first patient. In particular the function for image analysis can then be embodied for a follow-up analysis.

In particular by application of the function for image analysis, the medical comparison image dataset can be compared with the medical image dataset for the follow-up analysis.

In particular, by the application of the function for image analysis in the course of the follow-up analysis for example, a change in a lesion can be determined. In this case the lesion can be mapped in the medical comparison image dataset and/or in the medical image dataset. The lesion can for example be a tumor, an aneurysm and/or a change in an anatomical structure as in an osteoporosis or with COPD (acronym for Chronic Obstructive Pulmonary Disease) etc. The function for image analysis can be embodied for example to determine and/or to compare a size or a volume of the lesion in the medical comparison image dataset and the medical image dataset.

As an alternative or in addition the function for image analysis can be embodied to determine lesions that are only mapped in the medical image dataset or only in the medical comparison image dataset. In particular newly arising metastases can be determined in this way. In particular for example metastases can be determined that for example have disappeared under chemotherapy and/or radiation therapy.

The function for image analysis can thus be embodied for a longitudinal analysis or a temporal analysis of image datasets.

The inventors have recognized that image datasets that are suitable for a follow-up analysis by the function for image analysis can be determined by the method. Image datasets that map the same patient are in particular suitable in this case. These image datasets can be established or determined by carrying out the method described above.

According to a further example embodiment of the invention the medical image dataset is assigned to the medical comparison image dataset by a provisional assignment. In this case the method furthermore comprises a method step of correcting the provisional assignment between the medical image dataset and the medical comparison image dataset when the measure of difference is greater than or equal to the threshold value.

The provisional assignment allows the medical image dataset to be found automatically starting from the medical comparison image dataset. As an alternative or in addition the provisional assignment allows the medical comparison image dataset to be found automatically starting from the medical image dataset.

The provisional assignment can in particular be a provisional linkage of the medical image dataset and the medical comparison image dataset. The provisional linkage can be embodied in this case as described above with regard to the linkage. The provisional linkage can in particular refer to a storage location of the medical image dataset and/or the medical comparison image dataset. The provisional linkage can in this case be comprised by the medical image dataset and/or by the medical comparison image dataset. The provisional linkage in this case can comprise a link to the other imaging dataset in each case. In other words the provisional linkage comprised by the medical image dataset can comprise a link to the medical comparison image dataset. As an alternative or in addition the provisional linkage comprised by the medical comparison image dataset can comprise a link to the medical image dataset.

As an alternative or in addition the provisional assignment can be realized by a provisional common identification number. The provisional identification number in this case can be embodied as described above with regard to the identification number. The provisional identification number or provisional ID can in this case in particular be unique. The provisional ID can in this case be identical for the medical image dataset and the medical comparison image dataset provisionally assigned to one another. In particular, by a query about all image datasets with the same provisional ID, all image datasets assigned to one another by a provisional assignment can be determined. In this case the medical image dataset comprises the provisional ID. In this case the medical comparison image dataset comprises the provisional ID. All image datasets that comprise the same provisional ID are assigned to one another.

The method step of correcting the provisional assignment between the medical image dataset and the medical comparison image dataset is made when the measure of difference is greater than or equal to the threshold value.

In particular it can be assumed that the medical image dataset and the medical comparison image dataset relate to different patients when the measure of difference is greater than or equal to the threshold value. In particular the medical comparison image dataset can then map at least one part of the body of the first patient and the medical image dataset can map at least one part of the body of the second patient.

As an alternative it can be assumed that the mapped patient has changed greatly between the acquisition of the medical comparison image dataset and the medical image dataset when both image datasets map at least one part of the body of the first patient and the measure of difference is greater than or equal to the threshold value.

The correction of the provisional assignment in this case can in particular comprise a deletion of the provisional assignment. In particular this can comprise a deletion of the provisional linkage and/or of the provisional ID.

As an alternative or in addition the correction of the provisional assignment can be the provision of correction information for a user. The correction information can in this case specify that the provisional assignment has been identified as incorrect. In embodiments of the invention the user can confirm or reject this correction information. If confirmation information is received, the provisional assignment can be deleted. If rejection information is received, the provisional assignment can remain in place, even when the measure of difference is greater than or equal to the threshold value. The user in this case can for example be a doctor, a medical assistant etc.

The inventors have recognized that an incorrect assignment can be corrected by the correction of the provisional assignment. With the described method it can thus be checked whether the medical image dataset and the medical comparison image dataset actually relate to the same patient. The inventors have recognized that with a measure of difference that is greater than or equal to the threshold value it cannot be assumed that the medical image dataset and the medical comparison image dataset relate to the same patient. In order for example to prevent a follow-up image analysis being carried out based on image datasets that relate to different patients, the provisional assignment is corrected. Even when the measure of difference is large, although the medical image dataset and the medical comparison image dataset relate to the same patient, because the patient has changed greatly, the provisional assignment can be corrected as described above. The inventors have recognized that in this case automated follow-up image analyses possibly output incorrect results when the change to the patient is too great.

According to a further example embodiment of the invention the method furthermore comprises a method step of providing a warning signal when the measure of difference is greater than or equal to the threshold value.

The warning signal can in particular be an acoustic and/or an optical warning signal. In particular the user can be informed by the warning signal that the measure of difference is greater than or equal to the threshold value.

As an alternative or in addition the warning signal can comprise the correction information described above. The provision of the warning signal can thus comprise a provision of correction information.

The warning signal in this case can in particular be provided by a display unit. In other words the provision of the warning signal can comprise a display of the warning signal. The display unit can in this case in particular be a screen or a monitor. As an alternative or in addition the warning signal can be provided by a loudspeaker. In this case the warning signal can be provided by speech output. As an alternative or in addition the warning signal can comprise a warning tone, which is output with the loudspeaker. As an alternative or in addition the warning signal can be provided with a light. For example the light can glow red or flash when the measure of difference is greater than or equal to the threshold value.

The inventors have recognized that the user can be warned by the warning signal that a follow-up image analysis is possibly leading to incorrect results when the measure of difference exceeds the threshold value. Moreover, the inventors have recognized that by the warning signal the user can be alerted to a provisional assignment. The inventors have recognized that in this way it can almost be excluded that image datasets from different patients are incorrectly assigned to one another or linked to one another.

According to an optional aspect of the method the medical image dataset and the medical comparison image dataset comprise three-dimensional medical images.

In particular the image comprised by the medical image dataset is a three-dimensional medical image. In particular the image comprised by the medical comparison imaging dataset is a three-dimensional medical image.

The three-dimensional medical image in this case in particular maps the at least one part of the body of the first or second patient in three spatial directions. In this case the three-dimensional medical image comprises a plurality of voxels that are arranged in a voxel matrix. Each voxel in this case comprises a voxel value.

The three-dimensional medical image can in particular be a computed tomography image or a magnetic resonance tomography image or a tomosynthesis image or a positron emission tomography image or a single photon emission computed tomography image etc. In other words the medical image can have been acquired in particular with a computed tomography system or a magnetic resonance tomography system or a mammography system or a positron emission tomography system or a single photon emission computer tomography system or a C-arm system.

The inventors have recognized that the biometric data or the biometric comparison data is advantageously extracted from three-dimensional medical image data. The inventors have recognized that the biometric data or the biometric comparison data are then least susceptible to errors. The inventors have recognized that a two-dimensional projection of the biometric data or of the biometric comparison data can lead to a distortion.

At least one example embodiment of the invention optionally relates to a computer-implemented method for assigning a medical image dataset to a comparison image dataset depending on biometric data. The method comprises a method step of receiving the medical image dataset. The method furthermore comprises a method step of receiving a number of possible comparison imaging datasets. The method furthermore comprises an extraction of biometric data based on the medical image dataset. The method furthermore comprises an extraction of possible biometric comparison data based on each of the possible comparison imaging datasets. The method furthermore comprises a method step of determining measures of difference between the biometric data and each of the possible biometric comparison data. The method furthermore comprises a method step of selecting one or more medical comparison image datasets from the possible medical comparison image datasets based on the measures of difference. The method furthermore comprises a method step of assigning the medical image dataset to the one or more selected medical comparison image datasets.

The above description can be transferred by analogy to this embodiment of the invention. The embodiment of the invention can be combined with all aspects described above.

In the method step of selection in particular those medical comparison image datasets can be selected of which the measures of difference do not exceed the threshold value described above.

The inventors have recognized that the method can be used in order to assign the medical image dataset to the appropriate medical comparison image datasets from a larger set of comparison image datasets. The inventors have recognized that the method can thus also be applied when more than one medical comparison image dataset of a patient already has already been acquired.

The embodiments of the invention moreover relates to an assignment system for assigning a medical image dataset to a medical comparison image dataset depending on biometric data. The assignment system comprises an interface and a computing unit. The interface is embodied for receiving the medical image dataset. The interface is furthermore embodied for receiving at least one medical comparison image dataset. The computing unit is embodied for extracting biometric data based on the medical image dataset. The computing unit is furthermore embodied for extracting biometric comparison data based on the medical comparison image dataset. The computing unit is furthermore embodied for determining a measure of difference between the biometric comparison data and the biometric data. The computing unit is furthermore embodied for assigning the medical image dataset to the medical comparison image dataset, when the measure of difference does not exceed a threshold value.

Such an assignment system can in particular be embodied to carry out the previously described method for assigning a medical image dataset to a medical comparison image dataset depending on biometric data and its aspects. The assignment system is embodied to carry out this method and its aspects by the interface and the computing unit being embodied to carry out the corresponding method steps.

The embodiments of the invention also relates to a computer program product with a computer program as well as to a computer-readable medium. A largely software-based realization has the advantage that assignment systems already used previously can also be upgraded in a simple way by a software update in order to work in the way described. Such a computer program product, as well as the computer program, can where necessary comprise additional elements such as e.g. documentation and/or additional components, as well as hardware components, such as e.g. hardware keys (dongles etc.) for use of the software.

In particular the embodiments of the invention also relates to a computer program product with a computer program that is able to be loaded directly into a memory of an assignment system, with program sections for carrying out all steps of the method described above for assigning a medical image dataset to a medical comparison image dataset depending on biometric data and its aspects when the program sections are executed by the assignment system.

In particular the embodiments of the invention relates to a computer-readable storage medium on which program sections able to be read and executed by an assignment system are stored for carrying out all steps of the aforedescribed method for assigning a medical image dataset to a medical comparison image dataset depending on biometric data and its aspects when the program sections are executed by the assignment system.

The properties, features and advantages described above of the embodiments of the invention will become clearer and easier to understand in conjunction with the following figures and their descriptions. In this case the figures and descriptions are not intended to restrict the embodiments of the invention and its forms of embodiment in any way.

In different figures the same components are provided with corresponding reference characters. As a rule the figures are not true-to-scale.

FIG. 1 shows a first exemplary embodiment of a computer-implemented method for assigning a medical image dataset to a medical comparison image dataset depending on biometric data.

In a method step of receiving REC-1 a medical image dataset the medical image dataset is received by an interface SYS.IF. The medical image dataset in this case comprises a map or a medical image of a first or a second patient. The medical image in this case maps at least one part, in particular at least one part of the body of the first or second patient. In other words the medical image dataset maps the first or second patient. The part of the body can in this case be a thorax, an abdomen, a head, an arm or a leg of the first or second patient for example.

The medical image has been acquired with a medical imaging system. The medical imaging system can in particular be an x-ray system, a mammography system, a computed tomography system, a magnetic resonance tomography system, a C-arm system, an ultrasound system, a positron emission tomography system or a single photon emission computed tomography system etc. The medical image is a three-dimensional medical image. In alternate embodiments of the invention the medical image can be a two-dimensional medical image. The three-dimensional medical image comprises a plurality of voxels, which are arranged in a three-dimensional voxel matrix. Each voxel comprises a voxel value. The voxel value is a measured value, for example an intensity value, which represents a property of the material mapped in the voxel. When the medical image is two-dimensional the medical image comprises a two-dimensional pixel matrix with a plurality of pixels. Each pixel in this case is assigned a pixel value. The medical image is in particular in a DICOM format.

The medical image dataset is in particular anonymized or pseudonymized. In other words patient data in the medical image dataset is either removed or replaced by a pseudonym. As an alternative the patient data can be encrypted. It is thus not possible, based on the medical image dataset, to deduce an identity of the first or second patient. The patient data in this case is typically comprised by a DICOM header.

The medical image dataset is provided from a database. In other words the medical image dataset is received from the database with the interface SYS.IF. As an alternative the medical image dataset can be provided by the medical imaging system. As an alternative the medical image dataset can be provided by a user. The user is in this case in particular a doctor or a medical assistant. As an alternative the user can be the first or second patient.

The database is a Picture Archiving and Communications System, Acronym: PACS). As an alternative the database can be a Hospital Information System (acronym: HIS) or a Radiology Information System (acronym: RIS).

The database can be hosted on a local server. As an alternative the database can be hosted in a Cloud system.

In a method step of receiving REC-2 the medical comparison image dataset, the medical comparison image dataset is received with the interface SYS.IF.

The medical comparison image dataset is embodied similarly to the medical image dataset. The medical comparison image dataset likewise comprises a medical image, which was acquired with a medical imaging system. The medical imaging system in this case can be the same as or different from the medical imaging system with which the medical image of medical image dataset was acquired.

The medical image of the medical comparison image dataset maps the first patient. In other words the medical comparison image dataset maps the first patient. In this case at least one part, in particular part of the body of the first patient, is mapped. The part of the body can be the same as or different from the part of the body that the medical image dataset is mapping.

In this case the medical comparison image dataset is provided from the database or the medical imaging system or the user.

In a method step of extracting EXT-1 biometric data the biometric data is extracted based on the medical image dataset.

In this case the biometric data can already be comprised by the medical image dataset. Then the extraction EXT-1 of the biometric data comprises a reading out of the biometric data from the medical image dataset.

As an alternative the biometric data can be determined based on the medical image dataset. Then the extraction EXT-1 of the biometric data comprises a determination of the biometric data.

The biometric data describes a property of the first or second patient mapped in the medical image dataset. The property is in this case in particular unique to or characteristic of the patient. The biometric data is similar in this case to a fingerprint. The biometric data in this case for example describes an anatomical property or peculiarity of the first or second patient. The biometric data can for example specify when the first or second patient possesses only one kidney. As an alternative or in addition the biometric data can specify physical properties such as a size of the first or second patient. As an alternative or in addition the biometric data can specify an arrangement of anatomies for example of the organs and/or of the skeleton of the first or second patient.

In embodiments of the invention the biometric data comprises at least one anatomical landmark and/or at least one surface network of at least one anatomy of the part of the body mapped in the medical image dataset.

The anatomical landmark in this case specifies a position of an anatomy in the medical image of the medical image dataset. The position can in this case be specified in embodiments of the invention by a coordinate of the anatomical landmark in the medical image. The coordinate in a three-dimensional medical image is a triple. In other words the coordinate in a three-dimensional medical image comprises a triple of values, in which each value specifies the position of the anatomical landmark in the medical image in a spatial direction. When the medical image is two-dimensional, the coordinate comprises a pair of values. The anatomical landmark thus relates to an anatomy. The anatomy can in this case for example be one of the following anatomies: Center of the aortic arch, aortic root, branch of the arteria brachiocephalica, branch of the left arteria subclavia and the arteria vertebralis, branch of the right arteria subclavia and the arteria vertebralis, truncus coeliacus, left carotid artery, carina tracheae, heart, upper tip of the left kidney, upper tip of the right kidney, upper tip of the left lung, upper tip of the right lung, center of the liver, upper tip of the liver, pancreas, exit of the kidney artery, tip of the sternum, vertebral bodies: C7, T1, T2, T3, T4, T5, T6, T7, T8, T9, T10, T11, T12, L1. The biometric data can in particular comprise more than one anatomical landmark. Then two anatomical landmarks in each case relate to different anatomies.

The at least one anatomical landmark in the medical comparison image dataset or in the medical image dataset can have been determined for example as described in "Ghesu F C, Georgescu B, Zheng Y, Grbic S, Maier A, Hornegger J, Comaniciu D, "Multi- Scale Deep Reinforcement Learning for Real-Time 3D-Landmark Detection in CT Scans", IEEE Trans Pattern Anal Mach Intell. 2017".

As an alternative or in addition the biometric data comprises at least one surface network. The surface network describes in this case the surface of an anatomy of the first or second patient mapped in the medical image. The surface network thus relates to an anatomy of the first or second patient. The surface network in this case comprises more than one point on of the surface of the anatomy. In embodiments of the invention the surface network can comprise the points in the form of coordinates in the medical image. The surface network in this case comprises more than one coordinate. The coordinate is embodied in this case as described above. The anatomy to which the surface network relates can in this case for example be the left upper lobe of the lung, the left lower lobe of the lung, the right upper lobe of the lung, the right middle lobe of the lung, the right lower lobe of the lung, the heart, the aorta, the vertebral bodies. The at least one surface network can have been determined based on a segmentation of the anatomy in the medical image. The biometric data can comprise more than one surface network. In this case different surface networks relate to different anatomies or different regions of anatomies.

When the biometric data comprises more than one anatomical landmark and/or more than one surface network, the biometric data describes a spatial relationship between the anatomical landmarks and/or surface networks. The spatial relationship in this case describes a distance between the individual anatomical landmarks and/or surface networks. In this case the distance can in particular be specified in metric or Anglo-American units. The biometric data comprises the distance or the distances at least indirectly when it comprises the coordinates of the anatomical landmarks and/or surface networks. The spatial relationship can moreover describe a spatial arrangement of the anatomical landmarks and/or surface networks. The spatial arrangement can in this case in particular be given by the coordinates. The spatial arrangement describes the spatial location of the anatomical landmarks and/or surface networks in relation to one another in the two- or three-dimensional space. The spatial relationship can moreover take into consideration the shape of the surface network.

In a method step of extracting EXT-2 biometric comparison data the biometric comparison data is extracted based on the medical comparison image dataset.

As described above with regard to extracting EXT-1 of the biometric data, the extraction EXT-2 of the biometric comparison data can also comprise reading out or determination of the biometric comparison data from the medical comparison image dataset.

The biometric comparison data in this case, as regards the at least one part of the body of the first patient mapped in the medical comparison image dataset, can be embodied similarly to the biometric data. In particular, in embodiments of the invention, the biometric comparison data can comprise at least one anatomical landmark and/or at least one surface network. In this case, in embodiments of the invention, the at least one anatomical landmark and/or the at least one surface network can comprise a coordinate in the medical image comprised by the medical comparison image dataset. In this case the at least one surface network can in particular comprise more than one coordinate.

The biometric comparison data in this case comprises at least one anatomical landmark and/or at least one surface network, that relates to the same anatomy as the at least one anatomical landmark and/or surface network comprised by the biometric data.

In a method step of determining DET-1 a measure of difference, the measure of difference between the biometric comparison data and the biometric data is determined.

The measure of difference specifies in this case how greatly the biometric data differs from the biometric comparison data. The measure of difference is in this case the counterpart of a measure of similarity. The measure of difference specifies the difference for example as a real number or as a percentage or as a category. In this case the following applies: The greater the measure of difference, the greater the difference, the smaller the similarity of the biometric data and of the biometric comparison data. The category in this case can be one of a number of hierarchically structured categories. In this case the following applies: The higher the category is in the hierarchy, the greater is the difference, the less is the similarity between the biometric data and the biometric comparison data. The categories, in hierarchically ascending order, can be as follows for example: "Barely any differences", "medium", "great difference".

In a method step of assigning CON the medical image dataset to the medical comparison image dataset the medical image dataset is assigned to the medical comparison image dataset when the measure of difference does not exceed a threshold value.

The threshold value can in this case likewise be embodied as a real number or as a percentage or as a category. In this case the threshold value is embodied similarly to the measure of difference. The threshold value is determined empirically. As an alternative the threshold value can be determined by machine learning. The threshold value specifies how large the maximum measure of difference may be so that it can be assumed therefrom that the medical image dataset, just like the medical comparison image dataset, is mapping the first patient. When the measure of difference is below the threshold value or is less than the threshold value, it can be assumed that the medical image dataset and the medical comparison image dataset are mapping the same patient or comprise a medical image of the same patient. When the measure of difference is greater than or equal to threshold value, it can be assumed that the medical image dataset and the medical comparison image dataset are mapping different patients, or that they are mapping the same patient, who has changed greatly between the acquisition of the two image datasets. When the measure of difference and the threshold value are embodied in the form of a category, the measure of difference is below the threshold value when it is assigned to a category with a lower hierarchy than the threshold value.

FIG. 2 shows a second exemplary embodiment of a computer-implemented method for assigning a medical image dataset to a medical comparison image dataset depending on biometric data.

The method steps of receiving REC-1 the medical image dataset, of receiving REC-2 the medical comparison image dataset, of extracting EXT-1 the biometric data, of extracting EXT-2 the biometric comparison data, of determining DET-1 the measure of difference and of assigning CON the medical image dataset to the medical comparison image dataset are embodied similarly to the description in accordance with FIG. 1.

In this exemplary embodiment the method moreover comprises a method step of establishing DET-2 a registration between the biometric comparison data and the biometric data. The method step of determining DET-1 the measure of difference is undertaken in this case based on the registration.

When establishing DET-2 the registration, the biometric data and the biometric comparison data are put into a spatial context or into a spatial relationship to one another. In this way a spatial property, in particular a spatial relationship of the biometric data, is compared with a spatial property, in particular a spatial relationship, of the biometric comparison data.

This method step can in particular be carried out when the biometric data and the biometric comparison data each comprise more than one anatomical landmark and/or surface network. In this case the anatomical landmarks and/or surface networks of the biometric data are in a spatial relationship to one another that is specific for the patient mapped in the medical image dataset. Similarly the anatomical landmarks and/or surface networks of the biometric comparison data are in a spatial relationship to one another that is specific for the patient mapped in the medical comparison image dataset. When establishing the registration the anatomical landmarks and/or surface networks of the biometric data and of the biometric comparison data are put into a common spatial context.

In embodiments of the invention the registration is a rigid registration. In this case, during registration, the spatial relationship of the anatomical landmarks and/or surfaces of the biometric data and the spatial relationship of the anatomical landmarks and/or surfaces of the biometric comparison data are retained. In other words the spatial relationship is not changed by the registration. During the rigid registration the scale of the biometric data and the scale of the biometric comparison data are merely adapted to one another.

FIG. 3 shows a third exemplary embodiment of a computer-implemented method for assigning a medical image dataset to a medical comparison image dataset depending on biometric data.

The method steps of receiving REC-1 the medical image dataset, of receiving REC-2 the medical comparison image dataset, of extracting EXT-1 the biometric data, of extracting EXT-2 the biometric comparison data, of determining DET-1 the measure of difference and of assigning CON the medical image dataset to the medical comparison image dataset are embodied similarly to the description in accordance with FIG. 1. The method step of establishing DET-2 a registration is embodied in its most general form in accordance with the description for FIG. 2.

In the exemplary embodiment the method step of establishing DET-2 the registration comprises a method step of determining DET-3 anatomical landmarks and/or surface networks, which correspond to one another, in the biometric data and the biometric comparison data and a method step of transforming TRANS the anatomical landmarks and/or surface networks corresponding to one another into a common coordinate system.

In the method step of determining DET-3 the anatomical landmarks and/or surface networks which correspond to one another at least one pair of two anatomical landmarks or two surface networks is formed. In this case the anatomical landmarks and/or surface networks of a pair correspond to one another. One anatomical landmark or surface network of the pair is comprised by the biometric data. The other anatomical landmark or surface network of the pair is comprised by the biometric comparison data. Anatomical landmarks or surface networks which correspond to one another relate to the same anatomy. For example an anatomical landmark that relates to the xiphoid process in the medical image dataset corresponds to an anatomical landmark, which relates to the xiphoid process in the medical comparison image dataset. Similarly a surface network that relates to the surface of the heart in the medical image dataset corresponds to a surface network that relates to the surface of the heart in the medical comparison image dataset. In particular a number of pairs of anatomical landmarks and/or surface networks which correspond to one another can be determined when the biometric data and the biometric comparison data comprise more than one anatomical landmark and/or surface network.

In the method step of transforming TRANS the anatomical landmarks and/or surface networks which correspond to one another the anatomical landmarks and/or surface networks which correspond to one another are transformed into a common coordinate system. In this case the at least one anatomical landmark and/or the at least one surface network of the biometric data and the at least one anatomical landmark and/or the at least one surface network of the biometric comparison data each comprise one coordinate. The surface networks in this case can comprise more than one coordinate. When the biometric data and/or the biometric comparison data comprise more than one anatomical landmark and/or more than one surface network, the distance between the anatomical landmarks and/or surface networks is adapted during transformation TRANS to a scale of the common coordinate system. In this case the scale can be based on a metric unit. As an alternative the scale can be based on an Anglo-American unit. During transformation TRANS in particular the spatial relationship between the anatomical landmarks and/or surface networks of the biometric data and between the anatomical landmarks and/or surface networks of the biometric comparison data is retained or not changed.

During transformation TRANS, pairs of anatomical landmarks or surface networks which correspond to one another can be mapped to one another. "Map to one another" means that the two anatomical landmarks or surface networks are positioned at the same position in the common coordinate system. The other anatomical landmarks and/or surface networks are then positioned in accordance with their spatial relationship to the positioned anatomical landmark or surface network in the common coordinate system.

As an alternative the anatomical landmarks and/or surface networks can be positioned during transformation TRANS in such a way in the common coordinate system that the quadratic sum of all distances of the positions of the anatomical landmarks and/or surface networks which correspond to one another is minimal. In this case, as described above, the spatial relationships are retained in accordance with the biometric data and the biometric comparison data.

In the exemplary embodiment the method step of determining DET-1 the measure of difference comprises a method step of determining DET-4 a difference of the coordinates of the landmarks or surface networks which correspond to one another in the common coordinate system.

In this case, for each pair of anatomical landmarks or surface networks which correspond to one another, the distance between the positions of the two anatomical landmarks or surface networks is determined. The distance between the positions corresponds in this case to the difference between the coordinates. The distance or the difference in this case is in particular specified in a metric unit or in an Anglo-American unit.

The measure of difference in this case can be proportional to the sum of all quadratic differences or distances. As an alternative the measure of difference can be proportional to square root of the sum of all quadratic differences. The measure of difference in this case can in particular correspond to the standardized root of the sum of the quadratic distances. The standardization factor is in this case the number of pairs of anatomical landmarks or surface networks which correspond to one another.

In embodiments of the invention an influence of an anatomical landmark and/or of a surface network on the measure of difference depends on the temporal stability of the anatomical landmark or of the surface network. In this case the temporal stability of the anatomical landmark or of the surface network depends on the anatomy to which it relates. In other words the influence of two anatomical landmarks or surface networks which correspond to one another is equally great. The influence in this case predetermines a weighting of the difference between the coordinates when the measure of difference is determined. The weighting in this case can be specific for each pair of anatomical landmarks and/or surface networks. In particular temporally stable anatomical landmarks or surface networks are more heavily weighted than temporally unstable landmarks or surface networks. The measure of difference in this case can be proportional to the sum of all weighted quadratic differences or distances. The measure of difference can alternatively be proportional to the square root of the sum of all weighted quadratic differences. The measure of difference in this case can in particular correspond to the standardized square root of the sum of the weighted quadratic distances.

A temporally stable anatomical landmark or surface network is arranged almost spatially constant at any point in time relative to the patient. The temporally stable anatomical landmark describes a position of a specific bone for example. For example an anatomical landmark that relates to the xiphoid process is temporally constant.

A temporally unstable anatomical landmark is not constant in its position relative to the patient and in particular relative to a temporally stable anatomical landmark. A temporally unstable anatomical landmark can relate to an apex pulmonis for example. Depending on a breathing state of the first or second patient, the position of the apex pulmonis changes. The reason for a large difference between two temporally unstable anatomical landmarks corresponding to one another can either be that they relate to different patients or that the same patient has been mapped at different points in their breathing cycle in the corresponding imaging dataset.

FIG. 4 shows a fourth exemplary embodiment of a computer-implemented method for assigning a medical image dataset to a medical comparison image dataset depending on biometric data.

The method steps of receiving REC-1 the medical image dataset, of receiving REC-2 the medical comparison image dataset, of extracting EXT-1 the biometric data, of extracting EXT-2 the biometric comparison data, of determining DET-1 the measure of difference and of assigning CON the medical image dataset to the medical comparison image dataset are embodied similarly to the description in accordance with FIG. 1. The optional method step of establishing DET-2 a registration is embodied in its most general form in accordance with the description for FIG. 2. The optional method steps of determining DET-3 of landmarks and/or surface networks which correspond to one another, of transforming TRANS the landmarks and/or surface networks which correspond to one another and of determining DET-4 a difference of the coordinates of the landmarks or surface networks which correspond to one another are embodied in accordance with the description for FIG. 3.

The method moreover comprises a method step of applying APP-1 a trained function to the biometric comparison data and the biometric data. In this case the measure of difference is determined.

In embodiments of the invention the biometric data and the biometric comparison data have been registered in accordance with one of the embodiments of the method step of establishing DET-2 a registration. In an alternate embodiment of the invention the method step of establishing DET-2 a registration is not carried out. In an alternate embodiment the method step of applying APP-1 the trained function comprises the method step of establishing DET-2 a registration in one of its embodiments.

The method step of determining DET-4 the difference of the coordinates is carried out optionally.

The measure of difference is determined by applying APP-1 the trained function to the biometric data and to the biometric comparison data. In this case the trained function can in particular compare the spatial relationship of the anatomical landmarks and/or surface networks of the biometric data with the spatial relationship of the anatomical landmarks and/or surface networks of the biometric comparison data. On the basis thereof, by the application APP-1 of the trained function, the measure of difference, which specifies how likely it is that the biometric data and the biometric comparison data describe or relate to two different patients, can be determined.

Similarly to the description for FIG. 3, an influence of the anatomical landmarks or surface networks can depend on their temporal stability. The trained function in this case can weight an anatomical landmark and/or a surface network when determining DET-1 the measure of difference depending on their temporal stability. The greater the temporal stability, the greater is the weighting, the greater is the influence on the measure of difference.

FIG. 5 shows a fifth exemplary embodiment of a computer-implemented method for assigning a medical image dataset to a medical comparison image dataset depending on biometric data.

The method steps of receiving REC-1 the medical image dataset, of receiving REC-2 the medical comparison image dataset, of extracting EXT-1 the biometric data, of extracting EXT-2 the biometric comparison data, of determining DET-1 the measure of difference and of assigning CON the medical image dataset to the medical comparison image dataset are embodied similarly to the description in accordance with FIG. 1. The optional method step of establishing DET-2 a registration is embodied in its most general form in accordance with the description for FIG. 2. The optional method steps of determining DET-3 landmarks and/or surface networks corresponding to one another, of transforming TRANS the landmarks and/or surface networks corresponding to one another and of determining DET-4 a difference of the coordinates of the landmarks or surface networks corresponding to one another are embodied in accordance with the description for FIG. 3. The optional method step of applying APP-1 a trained function is embodied in accordance with the description for FIG. 4.

The method step of assigning CON the medical image dataset to the medical comparison image dataset comprises at least one of the following method steps:

Creating DET-5 a link between the medical image dataset and the medical comparison image dataset in a database;

Determining DET-6 a common identification number for the medical image dataset and the medical comparison image dataset;

Applying APP-2 a function for image analysis to the medical comparison image dataset and the medical image dataset.

In other words at least one of the said method steps is carried out when it can be assumed that the medical image dataset and the medical comparison image dataset are mapping the same, in particular the first, patient. When the measure of distance does not exceed the threshold value it can be assumed that the medical image dataset and the medical comparison image dataset are mapping the same patient.

In the method step of creating DET-5 the linkage between the medical image dataset and the medical comparison image dataset the medical image dataset and the medical comparison image dataset are linked in a database. In this case the medical image dataset and the medical comparison image dataset are held in the database. The database can in this case in particular be a PACS, a HIS or a RIS. The linkage is in this case a link or a reference to a storage location in the database. When the linkage is created a link to the storage location of the medical comparison image dataset in the database is thus added to the medical image dataset. As an alternative or in addition, when the linkage is created, a link to the storage location of the medical image dataset in the database is added to the medical comparison image dataset. When the medical image dataset or the medical comparison image dataset are retrieved or called by a user or by an application or use, the other imaging dataset in each case can be retrieved automatically via the link or via the linkage.

In the method step DET-6 of determining a common identification number (acronym: ID) a common ID is determined for the medical image dataset and the medical comparison image dataset. The common ID can then be assigned to the medical image dataset and the medical comparison image dataset. The common ID in this case is unique for the group of the image datasets assigned to one another. When the medical image dataset and the medical comparison image dataset are stored in the database the medical image dataset and the medical comparison image dataset can be provided via a database query for the common ID. All other image datasets assigned to the medical image dataset or the medical comparison image dataset can likewise comprise the common ID and are provided with the database query. All image datasets that relate to one patient are thus provided by a single database query. In this case an identification of the patient is not necessary. The common ID is independent of the possibly identifiable patient data. The common ID can in this case be a generic series of digits and/or numbers.

In the method step of applying APP-2 a function for image analysis the function for image analysis is applied to the medical image dataset and the medical comparison image dataset when the measure of difference is below the threshold value, i.e. when the medical image dataset and the medical comparison image dataset are mapping the same patient, in particular the first patient. The function for image analysis can in particular be embodied to compare the medical image of the medical image dataset with the medical image of the medical comparison image dataset. As an alternative or in addition the function for image analysis can be embodied to register the two medical images.

In embodiments of the invention the medical comparison image dataset has been determined at a time before the medical image dataset. By the application APP-2 of the function for image analysis a temporal change between the medical comparison image dataset and the medical image dataset is determined. In other words the function for image analysis is embodied for a longitudinal or temporal analysis of image data. In particular the function can be applied in the course of a follow-up examination or a subsequent examination of a patient, of the first patient for example. For example, by the application APP-2 of the function for image analysis, a change to a lesion can be observed or analyzed. The lesion can for example be a tumor and/or a tissue change and/or an aneurysm and/or an arteriosclerosis etc. The function for image analysis can in particular be embodied to recognize newly occurring lesions in the medical image dataset. As an alternative or in addition the function for image analysis can be embodied to recognize when a lesion is disappearing over time. The user can be informed about the change between the medical image dataset and the medical comparison image dataset. They can be informed by a screen output and/or by an output in a patient report about the change for example.

Figure 6:
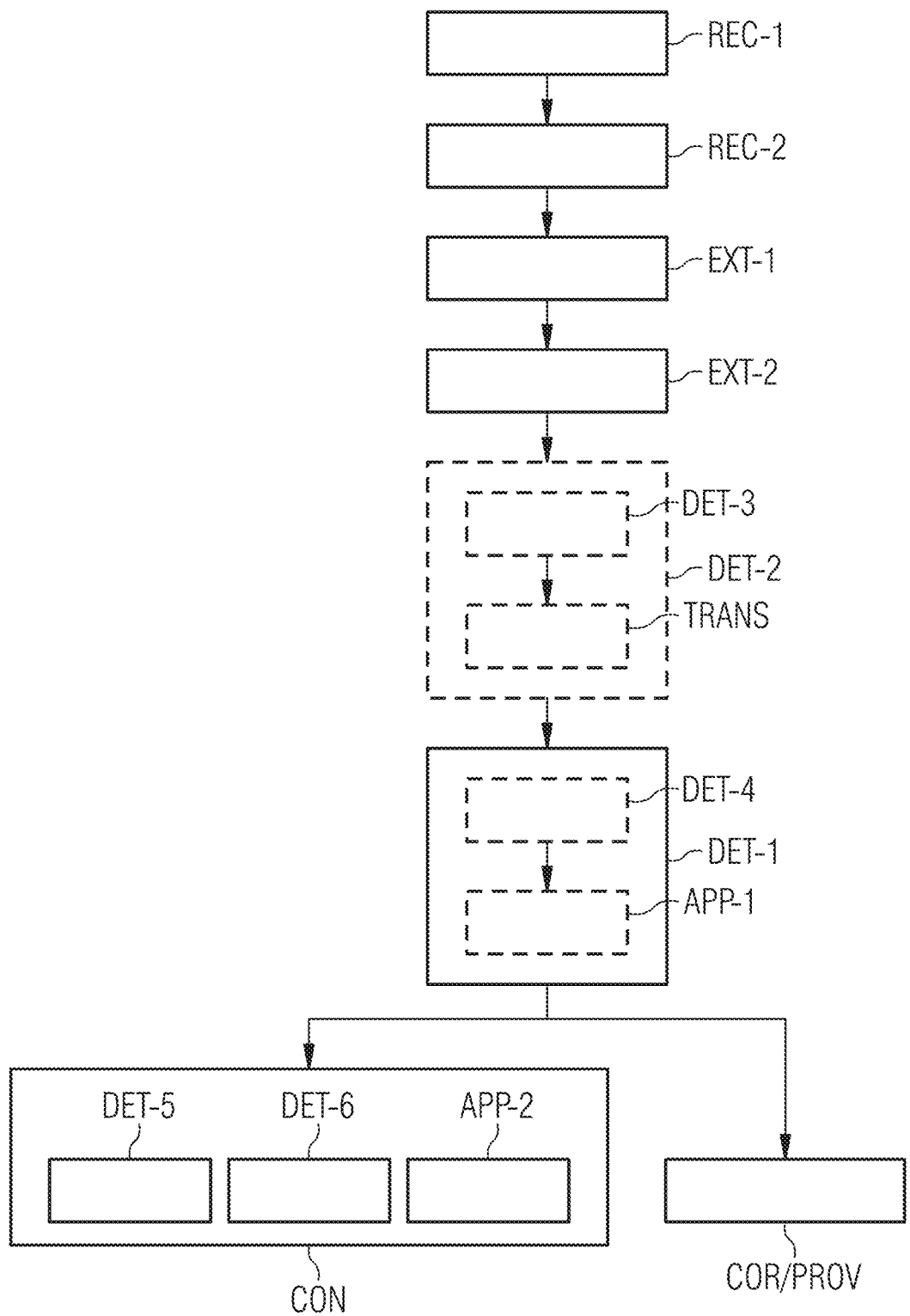
FIG. 6 shows a sixth exemplary embodiment of a computer-implemented method for assigning a medical image dataset to a medical comparison image dataset depending on biometric data.

FIG. 6 shows a sixth exemplary embodiment of a computer-implemented method for assigning a medical image dataset to a medical comparison image dataset depending on biometric data.

The method steps of receiving REC-1 the medical image dataset, of receiving REC-2 the medical comparison image dataset, of extracting EXT-1 the biometric data, of extracting EXT-2 the biometric comparison data, of determining DET-1 the measure of difference and of assigning CON the medical image dataset to the medical comparison image dataset are embodied similarly to the description in accordance with FIG. 1. The optional method step of establishing DET-2 a registration is embodied in its most general form in accordance with the description for FIG. 2. The optional method steps of determining DET-3 landmarks and/or surface networks corresponding to one another, of transforming TRANS of the landmarks and/or surface networks corresponding to one another and of determining DET-4 a difference of the coordinates of the landmarks or surface networks corresponding to one another are embodied in accordance with the description for FIG. 3. The optional method step of applying APP-1 a trained function is embodied in accordance with the description for FIG. 4. The method steps of creating DET-5 the linkage, of determining DET-6 the common identification number and of applying APP-2 the function for image analysis are embodied in accordance with the description for FIG. 5.

The method moreover comprises a method step of correcting COR a provisional assignment and/or a provision PROV of a warning signal when the measure of difference is greater than or equal to the threshold value.

In an embodiment of the invention the medical image dataset and the medical comparison image dataset are assigned to one another by a provisional assignment. The provisional assignment can be realized in this case in the form of a provisional linkage and/or a provisional identification number (acronym: ID). The provisional linkage and the provisional ID are embodied in this case in accordance with the description for the linkage and the common ID for FIG. 5.

When the measure of difference is greater than or equal to the threshold value, the provisional assignment is corrected in the method step of correcting COR the provisional assignment.

The correction COR of the provisional assignment in this case in embodiments of the invention comprises a deletion of the provisional assignment. In other words the correction COR of the provisional assignment then comprises a deletion of the linkage in the medical image dataset and the medical comparison image dataset. As an alternative or in addition the correction COR of the provisional assignment comprises a deletion of the provisional ID in the medical image dataset and/or the medical comparison image dataset.

As an alternative or in addition the correction COR of the provisional assignment comprises a provision of correction information for the user. The correction information in this case is displayed to the user with a display unit. The display unit can in particular be a screen or a monitor. The correction information comprises information about the measure of difference being greater than or equal to threshold value. In particular the correction information indicates to the user that the provisional assignment is probably incorrect. The user can confirm or reject the correction information via a user input. If the user confirms the correction information confirmation information is received. The receipt of the confirmation information can in this case bring about a deletion of the provisional assignment. If the user rejects the correction information, rejection information is received. Then the provisional assignment can be retained. The user can in particular reject the correction information when the medical image dataset and the medical comparison image dataset are mapping the same patient. The measure of difference can then still be greater than or equal to the threshold value if the patient has changed greatly between the two recordings of the medical image dataset and the medical comparison image dataset by a large change in weight for example. The user input can in particular be received via an input unit. The input unit can for example be a keyboard, a touch screen, a touchpad and/or a computer mouse etc.

As an alternative or in addition to the method step of correcting COR the provisional assignment, the method can comprise the method step of providing PROV a warning signal. The warning signal is provided when the measure of difference does not exceed the threshold value. The warning signal can in this case be optical and/or acoustic.

The warning signal in this case can in particular be the correction information described above. The correction information can be provided by the display unit. As an alternative the correction information can also be provided with a loudspeaker. The correction information can then be provided in the form of an announcement.

As an alternative or in addition the warning signal can be a warning tone or an acoustic signal. The acoustic signal can in this case in particular be provided with a loudspeaker.

As an alternative or in addition the warning signal can be an illumination, for example a flashing of a warning lamp. As an alternative the warning signal can be a change of a traffic light, for example from "green" to "red".

Figure 7:
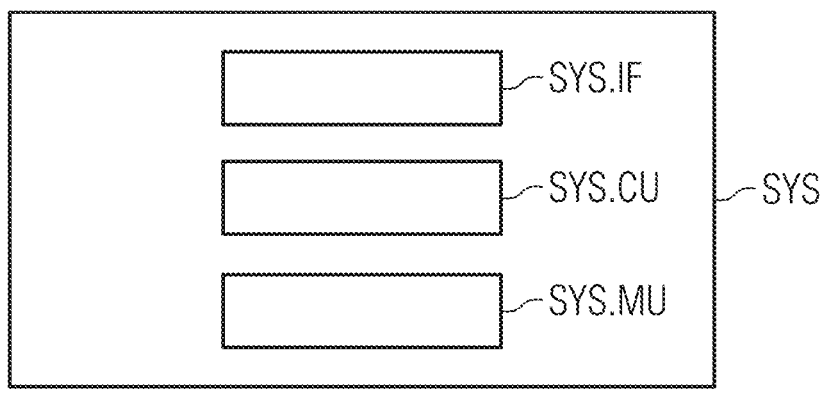
FIG. 7 shows an assignment system for assigning a medical image dataset to a medical comparison image dataset depending on biometric data.

FIG. 7 shows an assignment system SYS for assigning a medical image dataset to a medical comparison image dataset depending on biometric data.

The assignment system SYS shown for assigning a medical image dataset to a medical comparison image dataset depending on biometric data is embodied for carrying out a method according to embodiments of the invention for assigning a medical image dataset to a medical comparison image dataset depending on biometric data. The assignment system SYS comprises an interface SYS.IF, a computing unit SYS.CU and a memory unit SYS.MU.

The assignment system SYS can in particular be a computer, a microcontroller or an integrated circuit, IC. As an alternative the assignment system SYS can be a real or virtual computer network (a technical term for a real computer network is "cluster", a technical term for a virtual computer network is "Cloud"). The assignment system SYS can be embodied as a virtual system, which is executed on a computer or a real computer network or a virtual computer network (a technical term is "virtualization").

The interface SYS.IF can be a hardware or software interface (for example a PCI bus, USB or Firewire). The computing unit SYS.CU can comprise hardware and/or software elements, for example a microprocessor or what is known as an FPGA (Field Programmable Gate Array). The memory unit SYS.MU can be embodied as a Random Access Memory, (RAM) or as permanent mass storage (hard disk, USB stick, SD card, Solid State Disk (SSD)).

The interface SYS.IF can in particular comprise a plurality of sub interfaces, which carry out various method steps of the respective inventive method. In other words the interface SYS.IF can be embodied as a plurality of interfaces SYS.IF. The computing unit SYS.CU can in particular comprise a plurality of sub-processing units, which carry out various method steps of the respective inventive method. In other words the computing unit SYS.CU can be embodied as a plurality of computing units SYS.CU.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Where this has not occurred explicitly, but is sensible and in the spirit of the embodiments of invention however, individual exemplary embodiments, individual of their sub aspects or features, can be combined with or exchanged with one another without departing from the framework of current invention. Advantages of the embodiments of the invention described with regard to one exemplary embodiment also apply, where transferrable, without this being explicitly stated, to other exemplary embodiments.

What is claimed is:

1. A computer-implemented method, the method comprising:
    receiving a medical image dataset;
    receiving at least one medical comparison image dataset;
    extracting biometric data based on the medical image dataset;
    extracting biometric comparison data based on the medical comparison image dataset;
    determining a measure of difference between the biometric comparison data and the biometric data; and
    assigning the medical image dataset to the medical comparison image dataset when the measure of difference does not exceed a threshold value.

2. The method as claimed in claim 1, wherein at least one of
    (i) the medical comparison image dataset maps at least one part of a body of a first patient, or
    (ii) the medical image dataset maps at least one part of the body of the first patient or a second patient.

3. The method as claimed in claim 2, wherein
    the biometric data comprises at least one of at least one anatomical landmark or at least one surface network of at least one anatomy of the at least one mapped part of the body in the medical image dataset, and
    the biometric comparison data comprises at least one of at least one anatomical landmark or at least one surface network of at least one anatomy of the at least one mapped part of the body in the medical comparison image dataset.

4. The method as claimed in claim 3, wherein the at least one of the anatomical landmark or the surface network comprises at least one coordinate in the medical image dataset or in the medical comparison image dataset.

5. The method as claimed in claim 2, further comprising:
    establishing a registration between the biometric comparison data and the biometric data, and
    the determining the measure of difference is based on the registration.

6. The method as claimed in claim 3, wherein the determining the measure of difference is based on a temporal stability of the at least one of at least one anatomical landmark or at least one surface network.

7. The method as claimed in claim 3, further comprising:
    establishing a registration between the biometric comparison data and the biometric data, and
    the determining the measure of difference is based on the registration.

8. The method as claimed in claim 1, further comprising:
establishing a registration between the biometric comparison data and the biometric data, and
the determining the measure of difference is based on the registration.

9. The method as claimed in claim 8, wherein
the establishing the registration includes,
   determining at least one of anatomical landmarks or surface networks corresponding to one another in the biometric comparison data and the biometric data, and
   transforming the at least one of anatomical landmarks or surface networks corresponding to one another into a common coordinate system, and
the determining the measure of difference includes,
   determining a difference of the coordinates of the at least one of anatomical landmarks or surface networks corresponding to one another in the common coordinate system.

10. The method as claimed in claim 8, wherein the establishing the registration of the biometric comparison data and of the biometric data comprises a rigid registration.

11. The method as claimed in claim 1, wherein the determining the measure of difference comprises:
applying a trained function to the biometric comparison data and the biometric data to determine the measure of difference.

12. The method as claimed in claim 1, wherein the assigning the medical image dataset comprises at least one of:
   creating a linkage between the medical image dataset and the medical comparison image dataset in a database;
   determining a common identification number for the medical image dataset and the medical comparison image dataset; or
   applying a function for image analysis to the medical comparison image dataset and the medical image dataset.

13. The method as claimed in claim 12, wherein
the medical comparison image dataset has been acquired at a time before the medical image dataset, and
the applying the function for image analysis to the medical comparison image dataset and the medical image dataset includes determining a temporal change between the medical comparison image dataset and the medical image dataset.

14. The method as claimed in claim 13, further comprising:
providing a warning signal when the measure of difference is greater than or equal to threshold value.

15. The method as claimed in claim 1, wherein the medical image dataset is assigned to the medical comparison image dataset by a provisional assignment, the method further comprising:
correcting the provisional assignment between the medical image dataset and the medical comparison image dataset when the measure of difference is greater than or equal to the threshold value.

16. The method as claimed in claim 15, further comprising:
providing a warning signal when the measure of difference is greater than or equal to threshold value.

17. The method as claimed in claim 1, further comprising:
providing a warning signal when the measure of difference is greater than or equal to threshold value.

18. A non-transitory computer-readable storage medium comprising program sections, when executed by an assignment system, cause the assignment system to perform the method of claim 1.

19. An assignment system comprising:
an interface configured to receive a medical image dataset and at least one medical comparison image dataset; and
a computing unit, the computing unit configured to
extract biometric data based on the medical image dataset,
extract biometric comparison data based on the medical comparison image dataset,
determine a measure of difference between the biometric comparison data and the biometric data, and
assign the medical image dataset to the medical comparison image dataset when the measure of difference does not exceed a threshold value.

20. An assignment system comprising:
an interface configured to obtain a medical image dataset and at least one medical comparison image dataset; and
at least one processor configured to cause the assignment system to,
extract biometric data based on the medical image dataset,
extract biometric comparison data based on the medical comparison image dataset,
determine a measure of difference between the biometric comparison data and the biometric data, and
assign the medical image dataset to the medical comparison image dataset when the measure of difference does not exceed a threshold value.

* * * * *